(12) United States Patent
Liotta et al.

(10) Patent No.: US 11,074,998 B1
(45) Date of Patent: Jul. 27, 2021

(54) REAL-TIME DELIVERY OF MEDICAL TEST DATA TO PORTABLE COMMUNICATIONS DEVICES

(75) Inventors: Lance A. Liotta, Bethesda, MD (US); Tyson Liotta, Gaithersburg, MD (US)

(73) Assignee: INSTANTDX, LLC, Gaithersburg, MD (US)

( * ) Notice: Subject to any disclaimer, the term of this patent is extended or adjusted under 35 U.S.C. 154(b) by 1251 days.

(21) Appl. No.: 10/130,402

(22) PCT Filed: Nov. 14, 2000

(86) PCT No.: PCT/US00/42116
§ 371 (c)(1),
(2), (4) Date: Oct. 17, 2002

(87) PCT Pub. No.: WO01/37110
PCT Pub. Date: May 25, 2001

Related U.S. Application Data

(60) Provisional application No. 60/165,500, filed on Nov. 15, 1999.

(51) Int. Cl.
*G16H 20/10* (2018.01)
*G16H 40/67* (2018.01)
*G16H 40/20* (2018.01)
*G16H 10/40* (2018.01)
*G16H 50/30* (2018.01)

(52) U.S. Cl.
CPC .......... *G16H 20/10* (2018.01); *G16H 10/40* (2018.01); *G16H 40/20* (2018.01); *G16H 40/67* (2018.01); *G16H 50/30* (2018.01)

(58) Field of Classification Search
CPC .............................................. G06Q 50/22–24
USPC .......................................................... 705/2–3
See application file for complete search history.

(56) References Cited

U.S. PATENT DOCUMENTS

| | | | |
|---|---|---|---|
| 4,041,174 A * | 8/1977 | Sapse | 514/330 |
| 4,852,570 A * | 8/1989 | Levine | 600/301 |
| 5,441,047 A | 8/1995 | David et al. | |
| 5,737,539 A | 4/1998 | Edelson et al. | |
| 5,845,225 A | 12/1998 | Mosher | |
| 5,845,255 A * | 12/1998 | Mayaud | 705/3 |
| 5,867,688 A | 2/1999 | Simmon et al. | |
| 5,924,074 A * | 7/1999 | Evans | 705/3 |

(Continued)

OTHER PUBLICATIONS

Shabot, et al., "Inferencing Strategies for Automated Alerts on Critically Abnormal Laboratory and Blood Gas Data", Proceedings of the Thirteenth Annual Symposium on Computer Applications in Medical Care, Washington, D. C., Nov. 5-8, 1989.

(Continued)

*Primary Examiner* — Robert A Sorey
(74) *Attorney, Agent, or Firm* — Fay Sharpe LLP

(57) ABSTRACT

The present invention relates to a system and method for real-time delivery of medical tests and related data from laboratories (12) or similar sources (18) to portable communication devices such as mobile phones (14), text-enabled pagers (14) and web-enabled personal digital assistance (PDA's) (14) and other WAP devices (14). The subject system enables physicians to access test results remotely as soon as they become available. Also, the system allows the physician to develop an electronic prescription and submit the electronic prescription to a pharmacy using the portable communications device (14).

37 Claims, 19 Drawing Sheets

(56) References Cited

U.S. PATENT DOCUMENTS

| | | | |
|---|---|---|---|
| 5,942,986 A | | 8/1999 | Shabot et al. |
| 6,004,020 A | * | 12/1999 | Bartur .......................... 700/236 |
| 6,024,699 A | * | 2/2000 | Surwit et al. ................. 600/300 |
| 6,115,690 A | * | 9/2000 | Wong ........................... 705/7.27 |
| 6,305,377 B1 | | 10/2001 | Portwood et al. |
| 6,356,529 B1 | * | 3/2002 | Zarom .......................... 370/231 |
| 6,567,855 B1 | | 5/2003 | Tubbs et al. |
| 2002/0002513 A1 | | 1/2002 | Chiasson |
| 2002/0046346 A1 | | 4/2002 | Evans |
| 2002/0143563 A1 | | 10/2002 | Hufford et al. |
| 2002/0198473 A1 | | 12/2002 | Kumar et al. |
| 2003/0144884 A1 | | 7/2003 | Mayaud |
| 2011/0208534 A1 | * | 8/2011 | Liotta ................... G16H 20/10 705/2 |

OTHER PUBLICATIONS

Shabot, et al., "Real-Time Wireless Decision Support Alerts on a Palmtop PDA", Nineteenth Annual Symposium on Computer Applications in Medical Care, 1995, p. 174-177.

\* cited by examiner

REAL-TIME DELIVERY OF MEDICAL TEST DATA TO PORTABLE COMMUNICATIONS DEVICES

CROSS-REFERENCE TO RELATED APPLICATION

This application claims priority from and hereby incorporates by reference U.S. provisional application No. 60/165,500 filed Nov. 15, 1999.

BACKGROUND OF THE INVENTION

The present invention relates to a system and method for real-time delivery of medical tests and related data from laboratories or similar sources to portable communication devices such as mobile phones, text-enabled pagers and web-enabled personal digital assistance (PDA's). The subject system enables physicians to access test results remotely as soon as they become available. The subject system enables the physician to develop a prescription on a wireless device, such as a web enabled telephone, and submit the prescription electronically. The subject system exists as an interactive hub on the internet/world-wide-web (web) that exchanges information with portable devices. A special advantage is that the portable wireless devices do not need to be individually programmed or contain dedicated software—only a web browser is required. Also, the physician need not be within range of a particular computer installation. Instead, the system is operative anywhere wired and/or wireless internet access is available.

Healthcare is the largest single sector of the U.S. economy, consuming approximately $1 trillion annually, or 14% of the country's gross domestic product. In the U.S., the rise of managed care has forced healthcare facilities, physicians, and patients to focus on reducing the cost of care while maintaining the quality of care. In response, healthcare providers have been consolidating, and are turning towards information technology to reduce costs; and patients are using the Internet as a free and convenient source of health information.

Communications networks, such as the internet new mobile computing platforms, hold the potential to make the healthcare system more efficient by creating virtual relationships—bringing together physicians, payers, suppliers, and patients. The health and medical market is already one of the fastest growing areas of interest on the internet, making it the second largest vertical category behind financial services. A number of healthcare-focused portals such as drkoop.com and Healtheon provide content, commerce, and community. In addition, several online pharmacies such as PlanetRx and Drugstore.com provide online access to prescription medicines.

Mobile devices such as cellular phones, pagers, and palm computers have been used by physicians for years, providing them the benefits of mobility while traveling between office, hospital, and clinic. Physicians view these devices as indispensable to their work, and are familiar with the associated air time fees.

Current means of accessing lab results in the physician office environment are grossly inefficient, requiring physicians and labs to administer large amounts of faxed or couriered paper documents. Physicians phone the lab to retrieve test results and/or the lab sends a report by courier or fax to the physician's office. This usually happens the day after patient specimens are sent to the laboratory. This process imposes administrative burdens on both the physician's office and the lab as phone calls and faxes are exchanged. The physician, who is often mobile, must be contacted with the results in order to prescribe a treatment regimen. Meanwhile, the patient is anxiously awaiting the results with no access to information except by making a phone call to the physician's office.

With particular reference to mobile telephones, no prior systems are known to exist for receiving and transmitting medical information and/or transaction data. Mobile telephones have a limited display screen size and wireless data is transmitted to and from mobile telephones at rates that are slower than other wireless/wired devices. The limited screen size and buffer size require an elegant user interface for conveniently and effectively displaying all data and receiving input from a physician.

In light of the foregoing specifically noted deficiencies and others associated with conventional delivery of medical test data to physicians, a need has been identified for a system that increases the speed-accuracy-and security of medical test data delivery while providing better overall results.

SUMMARY OF THE INVENTION

In accordance with a first aspect of the present invention, a method for delivery and use of medical test data includes receiving medical test data related to at least one patient. The medical test data are generated by at least one medical laboratory in response at least one order of a physician. The medical test data are stored on a medical data server. The physician is notified by way of a portable communications device controlled by the physician that the medical test data are available on said medical data server. The medical test data are sent to the portable communications device controlled by said physician. Preferably, the portable communications device is a web-enabled mobile telephone.

One advantage of the present invention resides in the provision of a novel and non-obvious system for real-time delivery of medical test data to portable communications devices.

Another advantage of the present invention results from the provision of a novel and non-obvious system for real-time delivery of medical test data to a mobile telephone, wherein the phone can be used simultaneously for transmission/receipt of voice data.

Another advantage of the present invention is found in the provision of a system for real-time delivery of medical test data to portable communications devices, wherein a physician awaiting medical test data is notified as soon as the data are available.

A further advantage of the present invention is the provision of a system for real-time delivery of medical test data to portable communications devices, wherein a mobile physician is able to receive the data, interpret the data, and prescribe a treatment regiment without returning to his/her office or other base location.

Still another advantage of the present invention resides in the provision of a system for real-time delivery of medical test data to portable communications devices, wherein patients receive test results and associated information in a more timely and secure manner from physicians.

Yet another advantage of the present invention resides in the provision of a system for real-time delivery of medical test data to portable communications devices wherein the need to fax and/or courier test result documents is eliminated.

A further advantage of the present invention resides in the provision of a system for real-time delivery of medical test data, wherein a secure and convenient web-based interface is provided for physician access to the system.

Still other benefits and advantages of the present invention will become apparent to those of ordinary skill in the art to which the invention pertains upon reading and understanding this specification.

BRIEF DESCRIPTION OF THE DRAWINGS

The invention comprises various components and arrangements of components, and comprises various steps and arrangements of steps, preferred embodiments of which are illustrated in the accompanying drawings that form a part hereof and wherein.

DETAILED DESCRIPTION OF PREFERRED EMBODIMENTS

Figure 1:
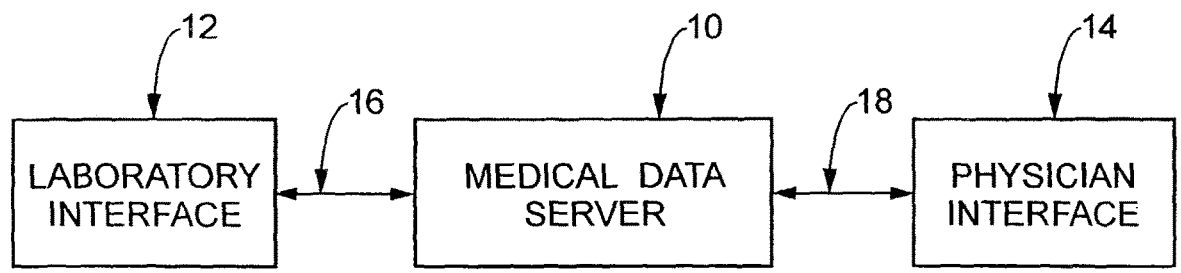
FIG. 1 is a simplified diagrammatic illustration of a system for real-time delivery of medical test data formed in accordance with the present invention.
Figure 2:
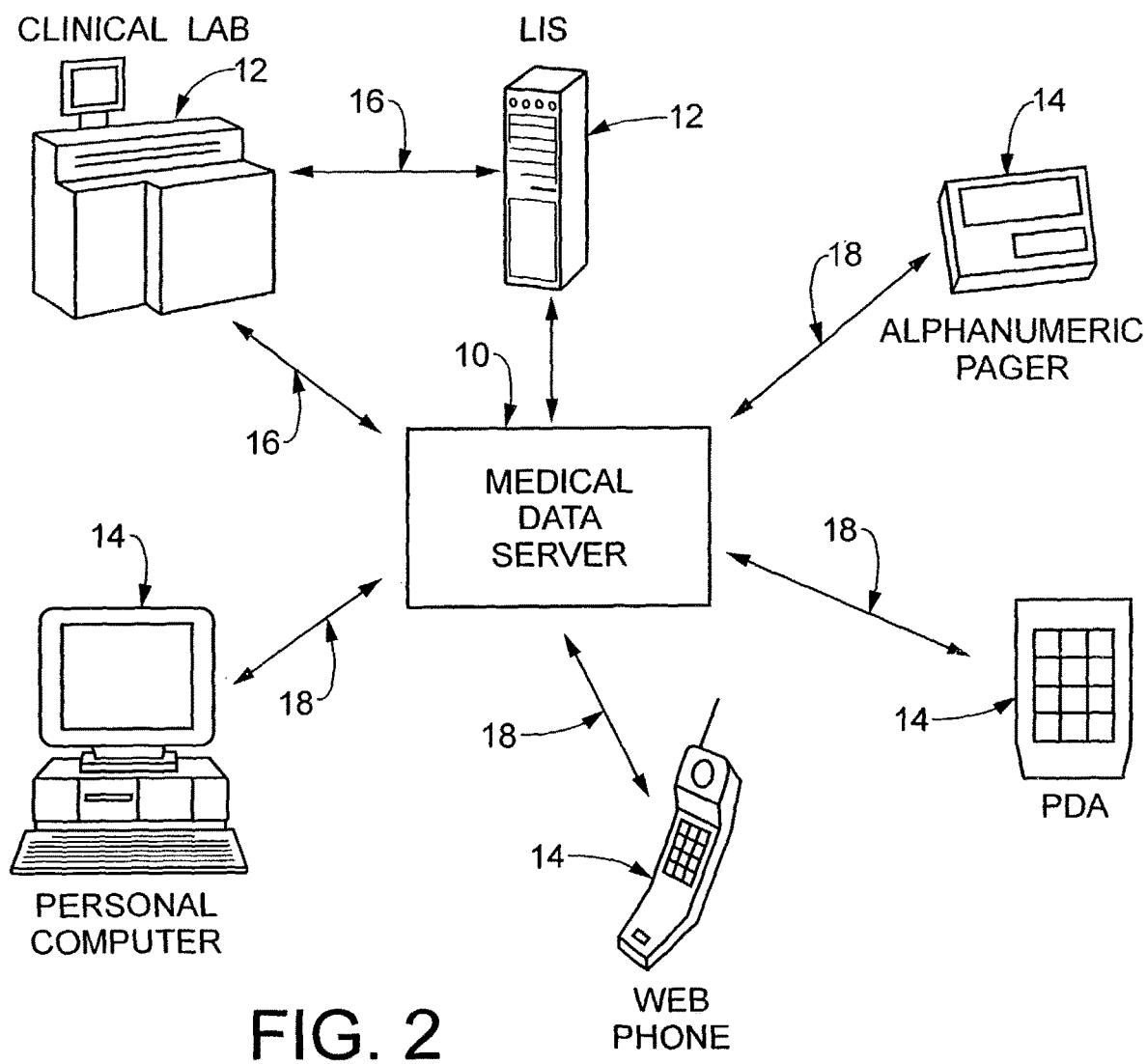
FIG. 2 is a more detailed diagrammatic illustration of the system of FIG. 1.

Referring now to the drawings, wherein the showings are for the purpose of illustrating preferred embodiments of the invention only and not limiting the invention in any way, FIGS. 1 and 2 illustrate a system for real-time delivery of medical test data to portable communications devices in accordance with the present invention. As illustrated in FIG. 1, the system comprises a medical data server computer 10, provided by any suitable computer, that receives medical test data such as lab reports and the like from a laboratory interface 12 and provides same to a physician interface 14. Data flow takes place using any suitable wired or wireless computer network(s). In a preferred embodiment, a hard-wired computer network 16, such as a dial-up network, an intranet, an extranet, the internet, etc., is utilized to move data between the laboratory interface 12 (i.e., the source of the medical test data) and the medical data server 10. In this preferred embodiment, it is most preferred that a wireless network 18, based upon cellular, PCS, or any other suitable wireless technology, be used to delivery medical test data from the medical data server 10 to the physician interface 14, which may be provided by any portable or fixed communications device.

Referring now to FIG. 2, the medical data server 10 is connected by the network 16 to one or medical testing data providers via laboratory interfaces 12 such as a clinical lab computer and a laboratory information server or system LIS. The physician interface 14 for one or more physicians to access and receive data from the medical data server 10 is provided by suitable portable wireless communications devices such as alphanumeric pagers, personal digital assistants (PDA's), web-enabled portable telephones, or other WAP (Wireless Application Protocol) devices and the like. A wired, fixed physician interface is also preferably provided by way of a personal computer or other fixed communications device. In such case, the network connection 18 could be provided by a dial-up or internet connection.

Figure 3:
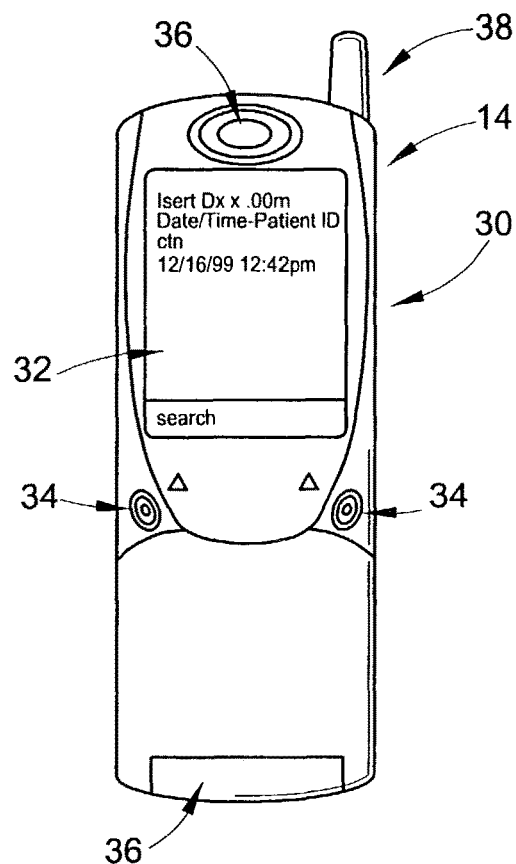
FIG. 3 illustrates one type of portable communications device to which medical test data is delivered in accordance with the present invention.

FIG. 3 illustrates an example of a suitable wireless physician interface 14 comprising a wireless web-enabled or other telephone 30 including a visual display 32 by which the physician receives text and other visual output from the device 30. The device 30 also comprises input means such as buttons 34 or the like, a microphone 36 for receipt of voice data/commands, a speaker for output of audible data, and an antenna for wireless connection to the medical data server 10.

Figure 4:
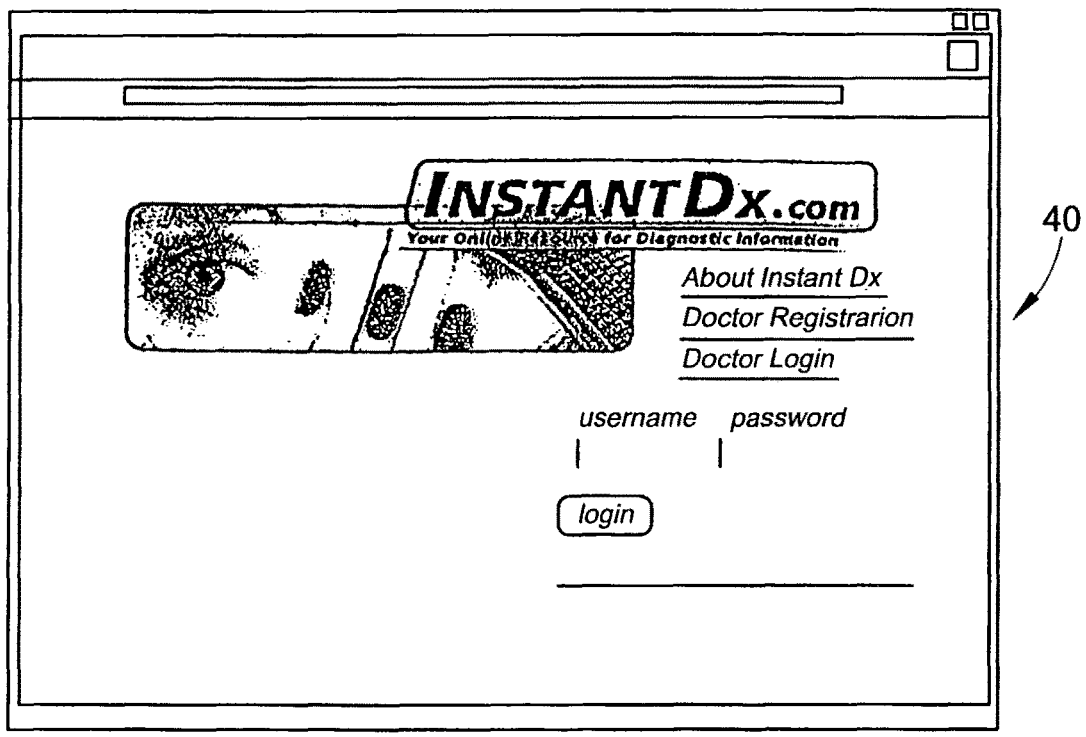
FIG. 4 illustrates a web-page physician interface to a medical data server that forms a part of a the system for real-time delivery of medical test data provided in accordance with the present invention.

FIG. 4 illustrates an example of a suitable physician interface 14 as provided by a personal computer. The illustrated web page 40 is presented to the physician by way of a monitor, screen, or other visual output device of the personal computer. The physician interacts with the web page using pointing devices, a keyboard, etc. and sends/receives data therethrough as is generally well known in the computing arts.

Figure 5:
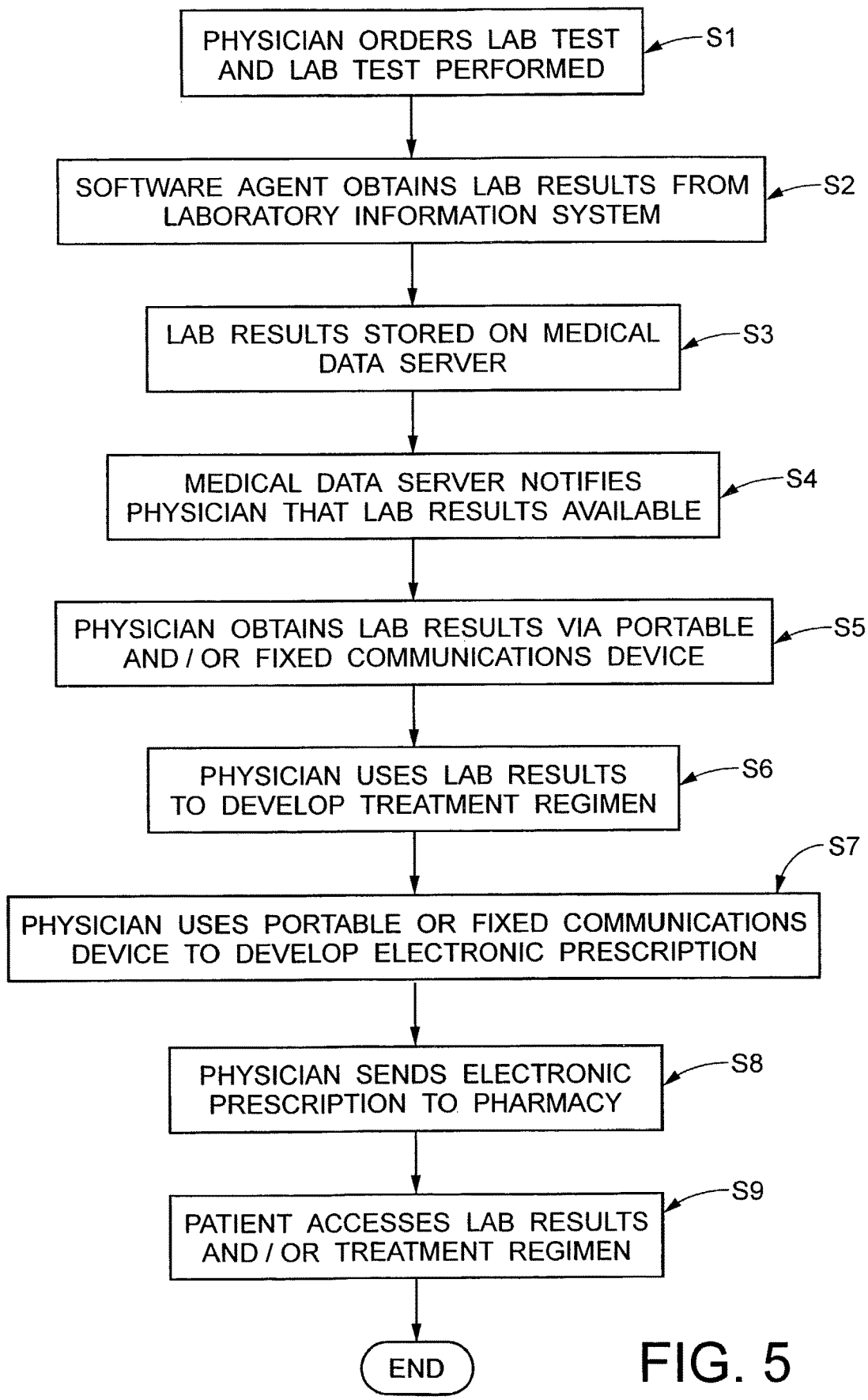
FIG. 5 is a flow-chart that discloses a method for real-time delivery of medical test data in accordance with the present invention.

Referring now to FIG. 5, a method for real-time delivery of medical test data to portable communications devices in accordance with the present invention is disclosed. The method comprises a step S1 including the physician ordering a lab test and performance of the lab test in a conventional manner. In a step S2, a software agent, installed on the laboratory information system LIS or other laboratory computer, obtains the lab results therefrom. In a step S3, the software agent sends the retrieved lab results, by way of the network 16, to the medical data server 10 where the data are stored.

Once the medical data server 10 has stored the newly obtained lab results or other medical test data, it performs a step S4 of notifying the physician that ordered the test(s) that the lab results are available. The step S4 is preferably carried out by sending a signal to a portable communications device carried by the physician such as a pager, cellular/PCS telephone, PDA, or the like.

In a step S5, the physician that ordered the test(s) obtains the lab results using one of the portable and/or fixed communications devices 18 by way of the network 18. Specifically, using one of the physician interface communications devices 14, the physician access the medical data server 10 which, in turn, supplies the lab results or other medical test data to the physician interface device 14.

The step S6 comprises the physician using the lab results obtained from the medical data server 10 to develop a treatment regimen which may include, for example, prescription of a pharmacological treatment.

In a step S7, the physician uses his/her portable or fixed communications device 14 to develop an electronic prescription, if necessary. The physician then uses the device 14 to send the electronic prescription to a pharmacy. This is accomplished by alternative means. In one example, the communications device 14 sends the electronic prescription to the medical data server 10 by way of the network 18. The medical data server 10 then connects to a computer at the pharmacy using a modem or any other suitable data network for the purpose of sending the electronic prescription to the pharmacy. In another embodiment, the physician uses his/her communications device 14 to connect directly with a pharmacy. For example, if the physician is using a communications device 14 that includes telephone capabilities, the physician can simply contact the pharmacist and provide an oral prescription or can transmit the electronic prescription data directly to a computer located at the pharmacy without sending the data through the medical data server 10.

In an optional step S9, a patient can access his/her own lab results and other medical test data, and review the physician's treatment regimen, by using a portable or fixed communications device 14 and connecting to the medical data server via network 18. In this manner, a patient can have instant and convenient access to his/her lab results and treatment regimen. Also, the physician and physician's staff are saved the administrative burden of retrieving this information for the patient.

Figure 6:
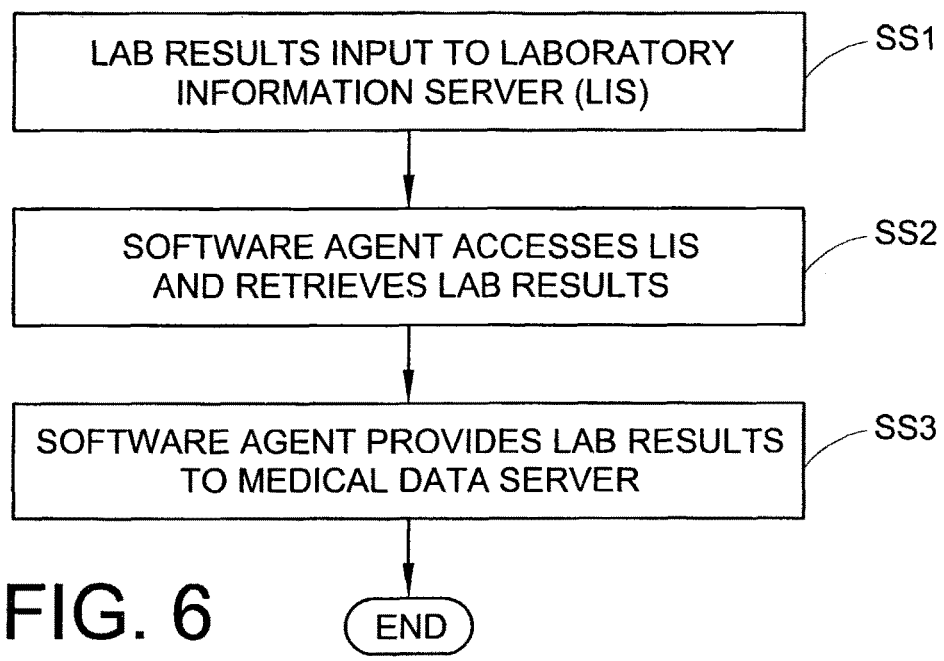
FIG. 6 is a flow chart that discloses a method for automatically obtaining medical test data from a laboratory information server and storing same on a medical data server in accordance with the present invention.
Figure 9:
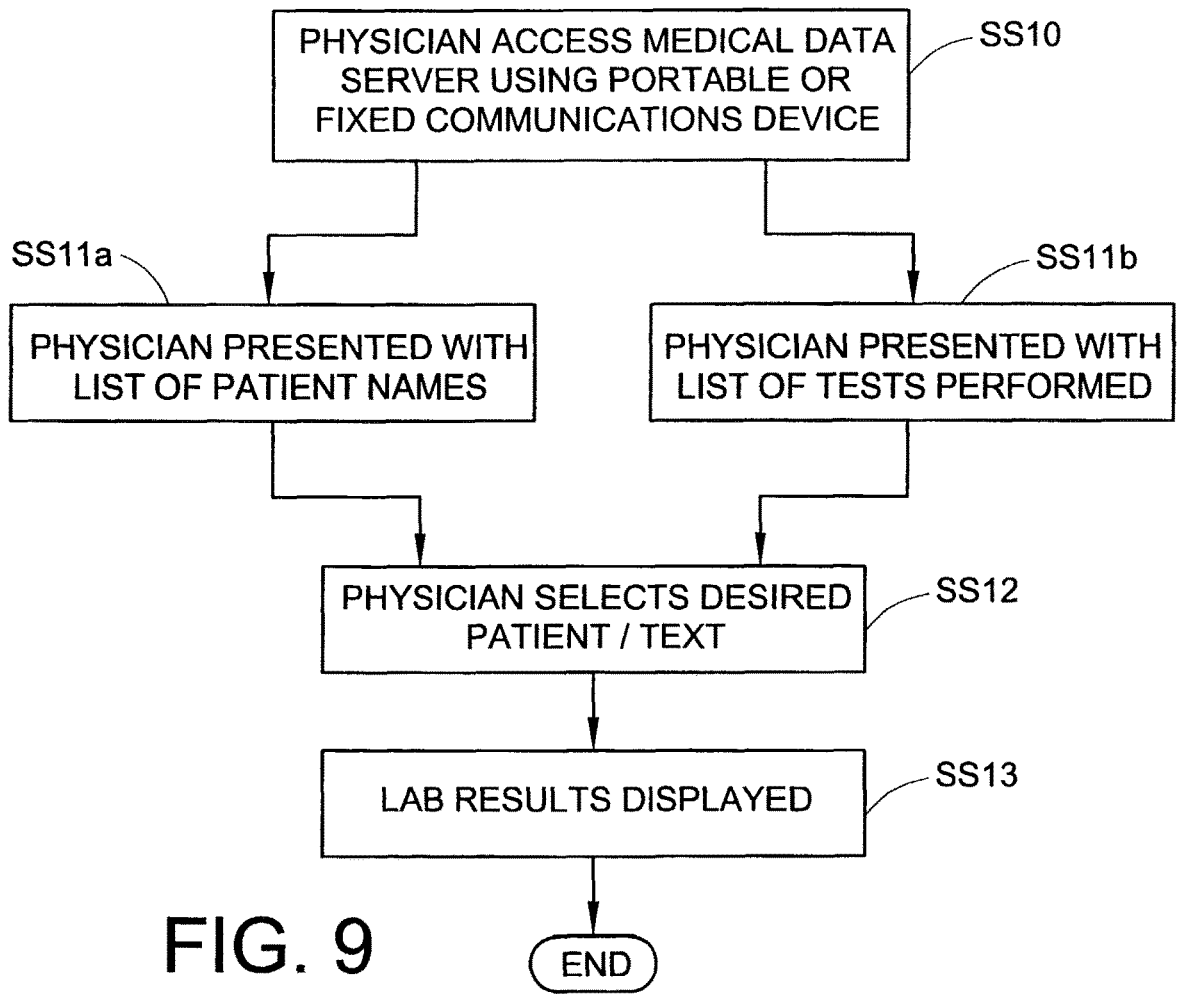
FIG. 9 is a flow chart that discloses a method by which a physician uses a communications device to receive medical test data from the medical data server.
Figure 7:
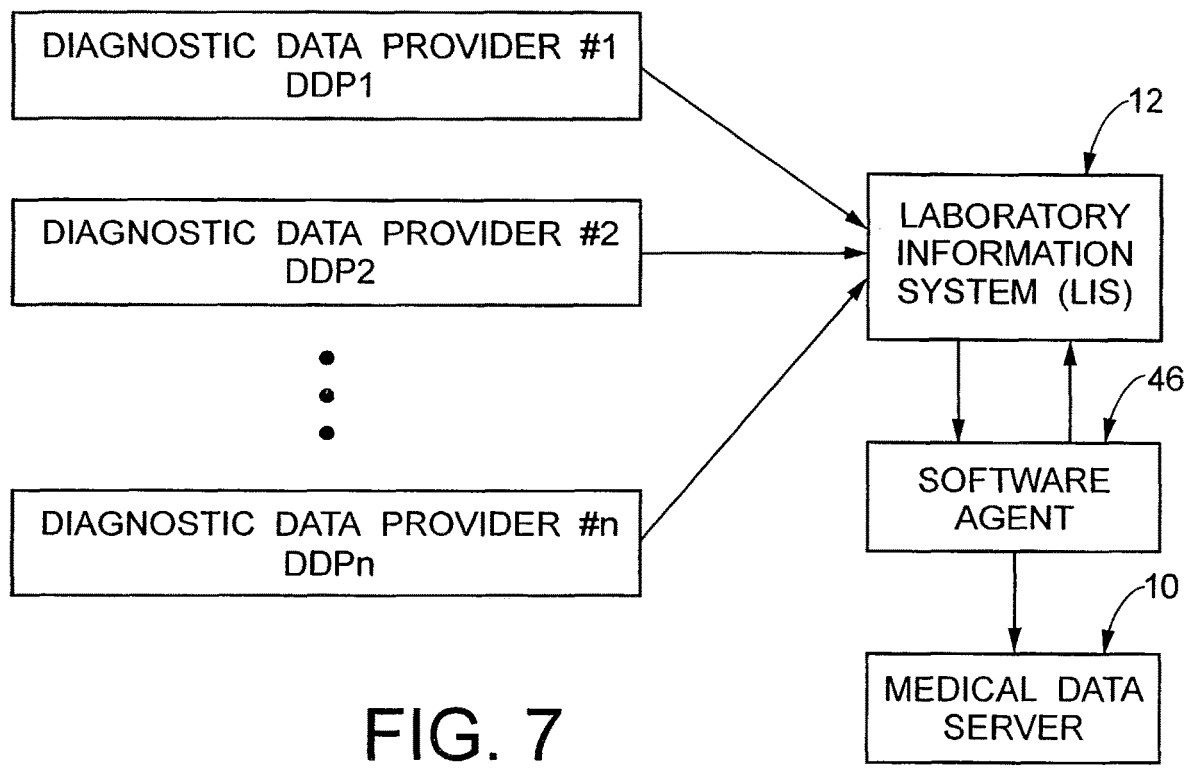
FIG. 7 diagrammatically discloses a method by which lab results and other medical test data are stored on a medical data server in accordance with the present invention.
Figure 8:
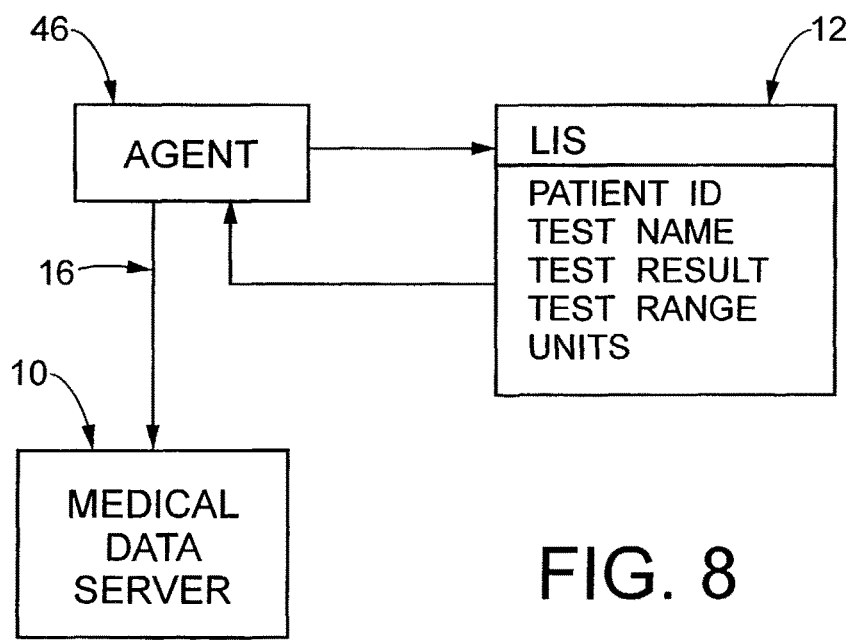
FIG. 8 diagrammatically illustrates operation of a software agent in accordance with the present invention for purposes of obtaining information from a laboratory information system (LIS) and storing same on a medical data server.
Figure 10A:
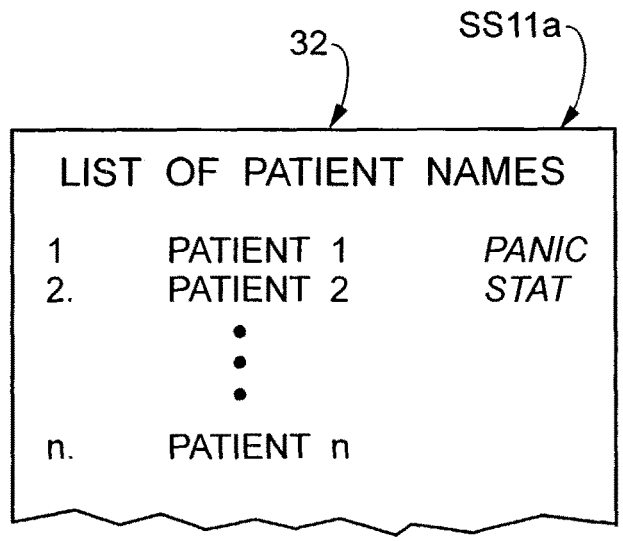
FIGS. 10A and 10B are respective first and second examples of a method for presenting medical test data to a physician by way of a portable or fixed communications device.
Figure 10B:
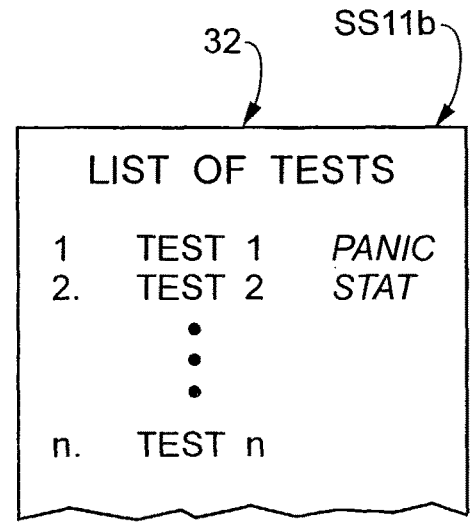

FIG. 6 discloses substeps related to steps S1-S3 of FIG. 5. In a substep SS1, the lab results or other medical test data are input to the laboratories computer system, referred to herein as a laboratory information system or server LIS. As shown in FIG. 7, this can be an automatic step wherein one or more diagnostic data providers DDP1,DDP2,DDPn are connected to the laboratory information system LIS and supply data thereto. In a step SS2, a software program, referred to herein as a software agent 46, accesses the laboratory information server LIS and retrieves the desired lab results and associated data. This is shown diagrammatically in FIGS. 7 and 8, wherein the agent 46 obtains from the laboratory information system LIS information such as the patient ID or name, test name, test result, test range, and units or measurement. The agent, of course, is programmed according to the specific laboratory information system LIS and its actions vary depending upon the data structures employed in the laboratory information system LIS. Finally, in a substep SS3, the software agent sends the retrieved lab results and/or other medical test data to the medical data server 10 by way of the network 16. Those of ordinary skill in the art will recognize that multiple software agents are used on multiple laboratory information servers LIS and are each sending data to the medical data server 10 for use by multiple physicians and in connection with treatment of multiple patients.

FIGS. 9-12 illustrate and discloses substeps and details related to steps S5 and S6 noted above, namely the steps related to the process by which a physician received lab results and/or other medical test data using a portable or fixed communications device. FIGS. 10A-12 diagrammatically illustrated a visual output display 32 of the portable communications device 30 noted above. In a substep SS10, the physician uses the device 30 to connect with and access the medical data server 10. In substeps SS11*a*,SS11*b*, the physicians, depending upon his/her preference, is presented with a list of patient names or a list of tests performed upon the physician's orders (see FIGS. 10A,10B, respectively). According to substep SS11*a*, and patient for whom a "panic" or "stat" lab result is indicated, that patient's name is listed before all other patients in the list displayed to the physician. Likewise, according to the substep SS11*b*, all "panic" and "stat" test results are displayed first to the physician.

Figure 11:
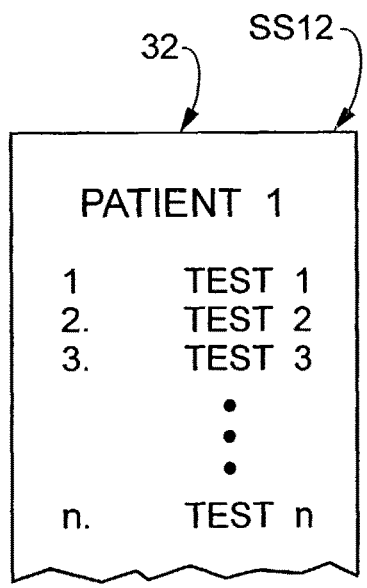
FIG. 11 is an example of a method by which the various test results available for a particular patient are set forth for a physician on his/her communications device.
Figure 12:
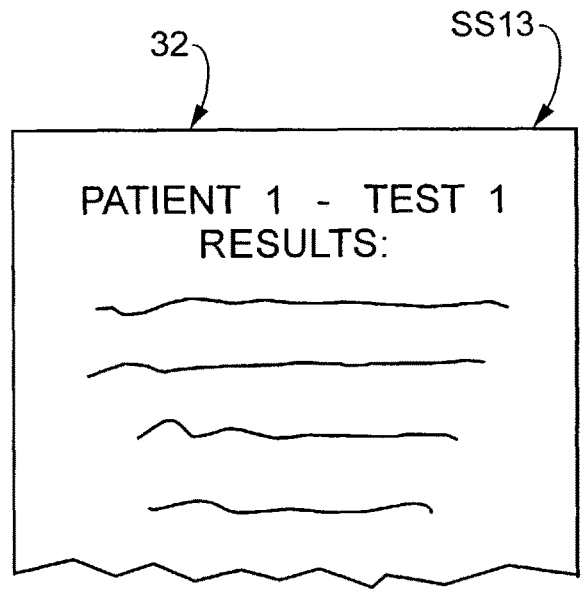
FIG. 12 is an example of medical test data displayed to a physician on his/her communications device for a particular patient and test.

Using the input buttons, a stylus, or other conventional input means associated with portable communications devices (or a mouse or keyboard if a PC is being used), in a substep SS12, the physician selects the patient or test. As shown in FIG. 11, for each patient selected, all tests associated with that patient are then displayed to the physician. The physician then selects the particular test in which he/she is interested and, in a substep SS13, these lab results are displayed to the physician as shown in FIG. 12.

Figure 13:
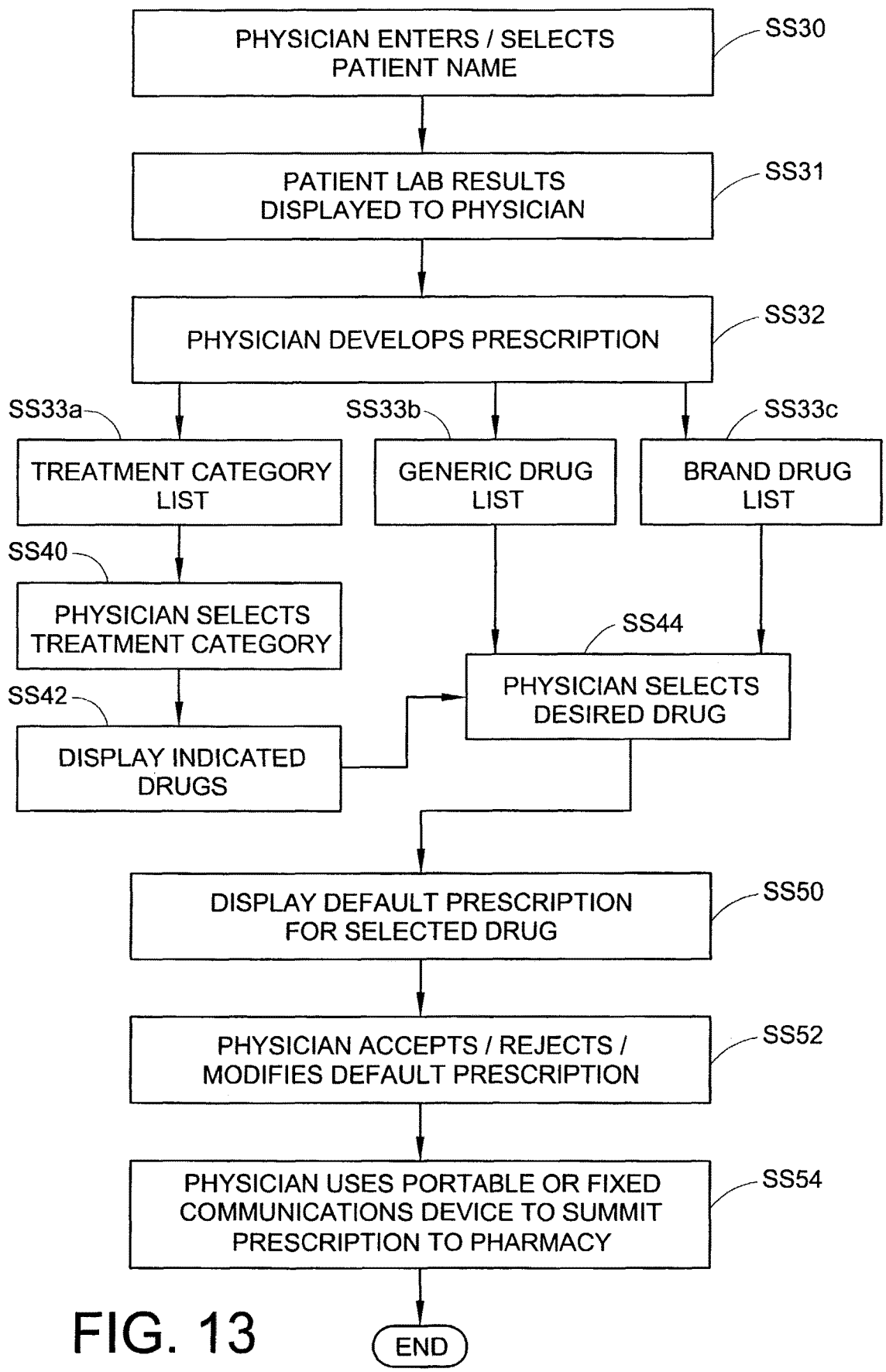
FIG. 13 is a flow chart that discloses a method by which a physician uses his/her communications device to prescribe pharmacological treatment to a patient using his/her communications device.

Referring now to FIG. 13, the details of the steps S7 and S8 are disclosed, namely the process by which a physician develops and sends to a pharmacy a prescription for a particular patient. In a substep SS30, the physician either enters or selects from a list the patient's name. Lab results associated with the subject patient are displayed to the physician as shown, e.g., in FIGS. 11 and 12. In a substep SS32, the physician develops a prescription for that patient using one of several procedures. In a substep SS33*a*, the physician is presented with a list of treatment categories including, e.g., infectious, cardiac, asthma, allergy, cough, etc. In a substep SS40, the physician selects one of the displayed treatment categories and in a substep SS42, a list of commonly indicated drugs for the selected category is displayed to the physician. Then in the substep SS44, the physician selects the desired branded or generic drug. In an alternative embodiment, the physician is presented with a list or generic (substep SS33*b*) or branded drugs (substep SS33*c*) and, in a substep SS44, the physician selects a desired drug for the patient being treated.

In any case, the process continues with substep SS50 that includes displaying a predefined default prescription for the selected drug to the physician. In a substep SS52, the physician either accepts the default prescription or modifies same. Finally, in a substep SS54, the physician uses the portable communications device 14 to send the electronic prescription to the pharmacy desired by the patient as specified in advance.

In a most preferred embodiment, the medical data server 10 and/or the portable device 14 remember(s) previous preferences of each physician (this information is preferably stored in the server 10 to minimize memory usage in the portable device 14). Thus, for example, a physician's preferences concerning output format of test results or pharmaceuticals prescribed in connection with particular test results are stored at the server 10 or in the portable device 14. These stored preferences are presented to the physician at the portable device 14 or other physician interface as a default to minimize required input from the physician. For example, if a physician typically specifies "dispense as written" (DAW) for prescriptions, this information is stored and presented as a default for all prescriptions. Further, it is also preferred that the medical data server 10 and/or the device 14 aid in patient care and compliance by notifying the physician of potential pharmaceutical conflicts or contraindications. In one embodiment, the medical data server 10 receives information from pharmacies concerning whether a patient has filled or refilled prescriptions as specified. If the patient has not complied, the physician is notified by way of the portable device 14. Of course, the medical data server 10 can interface with or include known expert systems to aid in diagnosis, treatment, and patient compliance. This information is also transmitted to the wireless device 14 upon request or automatically. For example, in the event a physician attempts to prescribe a pharmaceutical or dosage of same that is deemed inappropriate by the expert system, the physician is notified and is required to confirm his/her actions. In another example, when a physician prescribes a pharmaceutical that requires the patient submit to additional lab testing, the medical data server 10 sends a message to the portable device 14 periodically, on a select date or otherwise to remind the physician of same.

Referring now to FIGS. 14-23, use of the mobile web-enabled phone 30 to provide real-time medical test data to a physician is illustrated. The transaction is carried out by sending wireless data between the server 10 to the mobile device 30. At the mobile device, the physician preferably receives data by way of the visual output display 32, and preferably inputs data to the mobile device 30 by way of the one or more input buttons 34.

Figure 15:
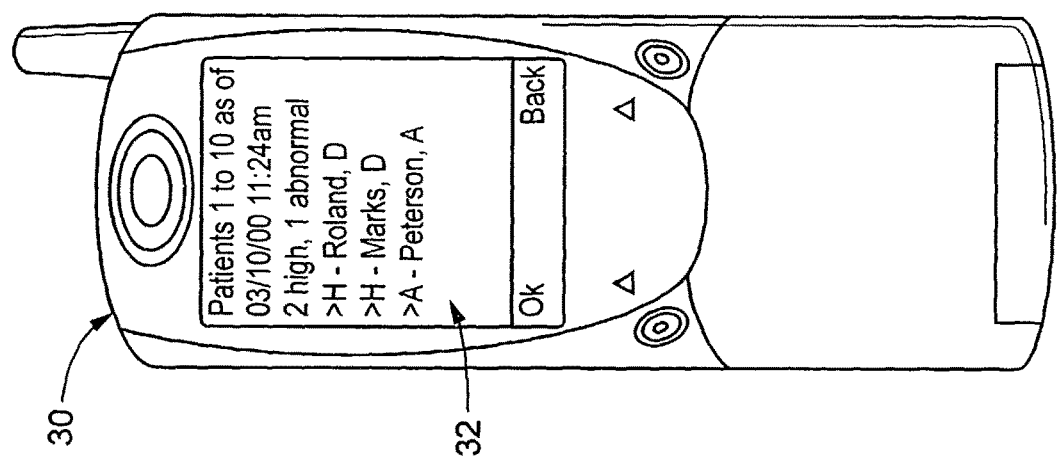
Figure 14:
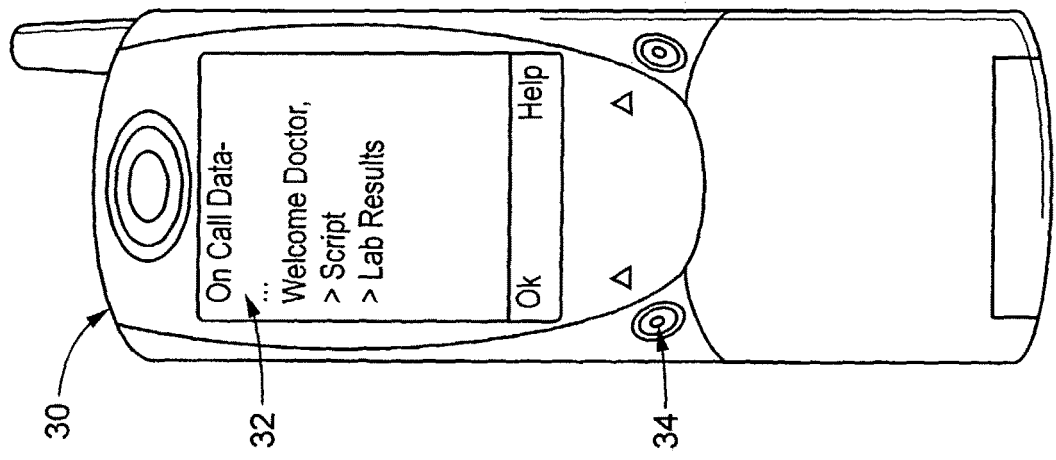
Figure 19:
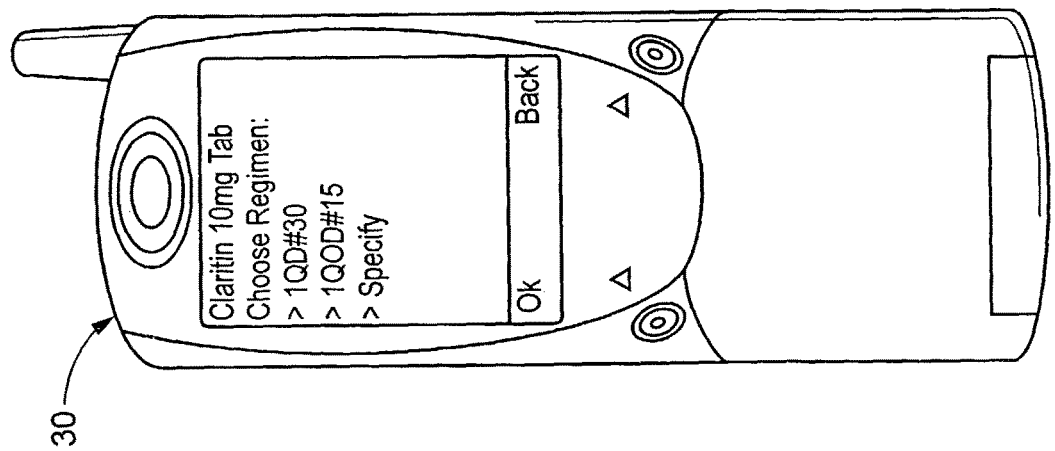
Figure 26:
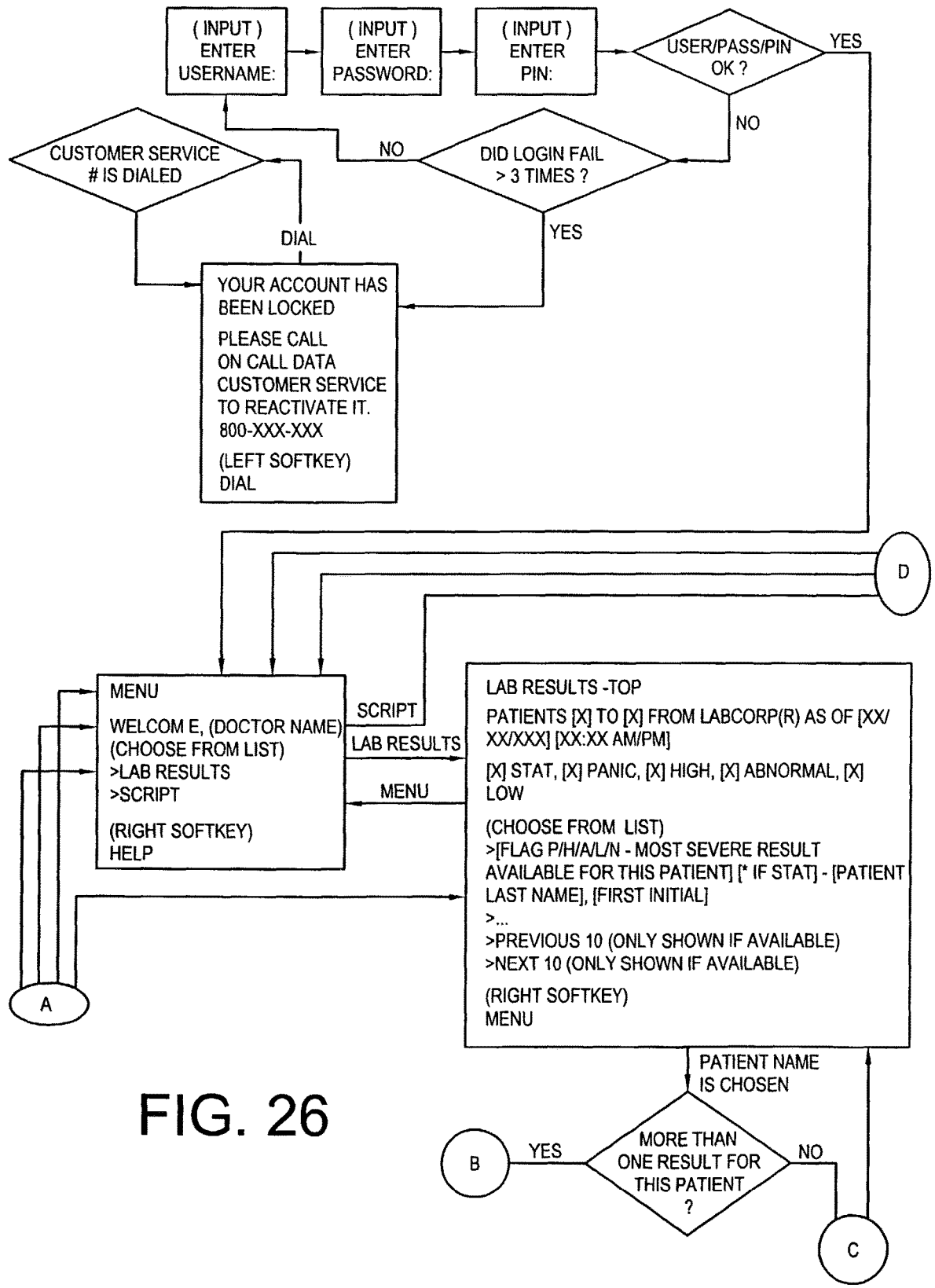

FIG. 14 illustrates a welcome display from which the physician chooses to write a prescription or receive lab results. In the present example, the physician chooses to review lab results. As shown in FIG. 15, the physician is presented with an overview of lab results for his/her patients. As noted above, patients are listed in order of lab result severity with quality designations such as "H" for high results, "L" for low results, "A" for abnormal results, "N" for normal, etc. The physician is able to use the input buttons 34 or other input means to scroll through the list and select a patient from the list (see also FIG. 26).

Figure 16:
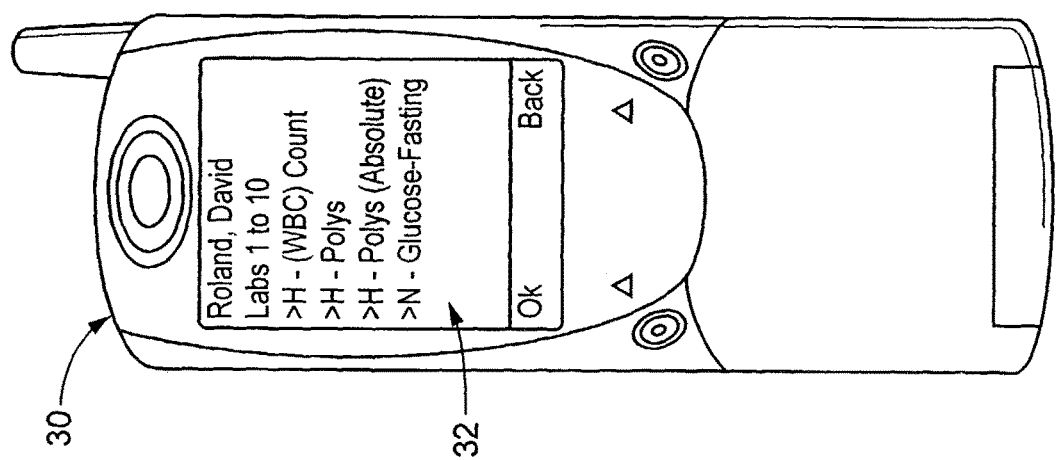
FIGS. 14-25 illustrate real-time delivery of medical test data to a portable telephone in accordance with the present invention and a physician's use of a portable telephone to write and send prescription data to a pharmacy in accordance with the present invention; and, FIGS. 26-33 together define a flow chart that discloses the methods illustrated in FIGS. 14-31.

As shown in FIG. 16, the physician has selected patient "Roland, David" and is presented with a list of lab results for the patient, again with the quality designation for each test an in order of severity. Here, the physician selects the first listed result "H-(WBC) Count."

Figure 17:
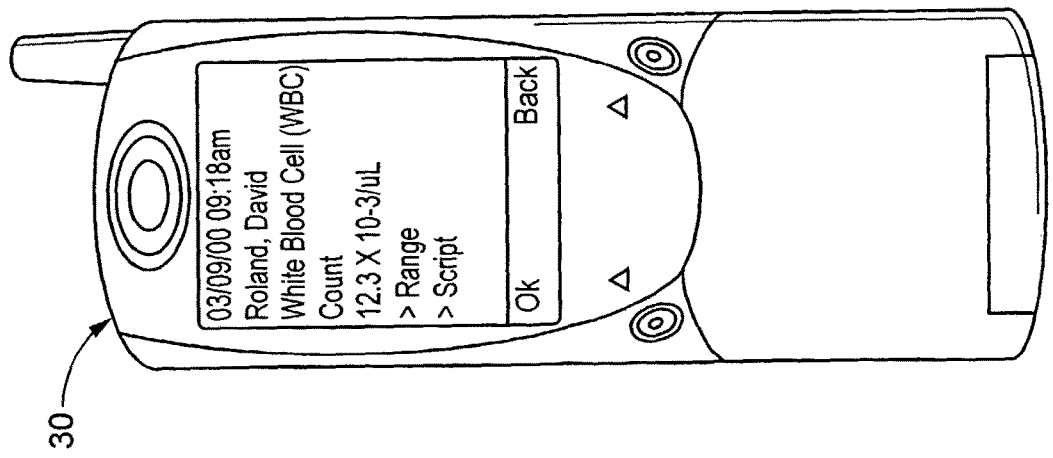
Figure 27:
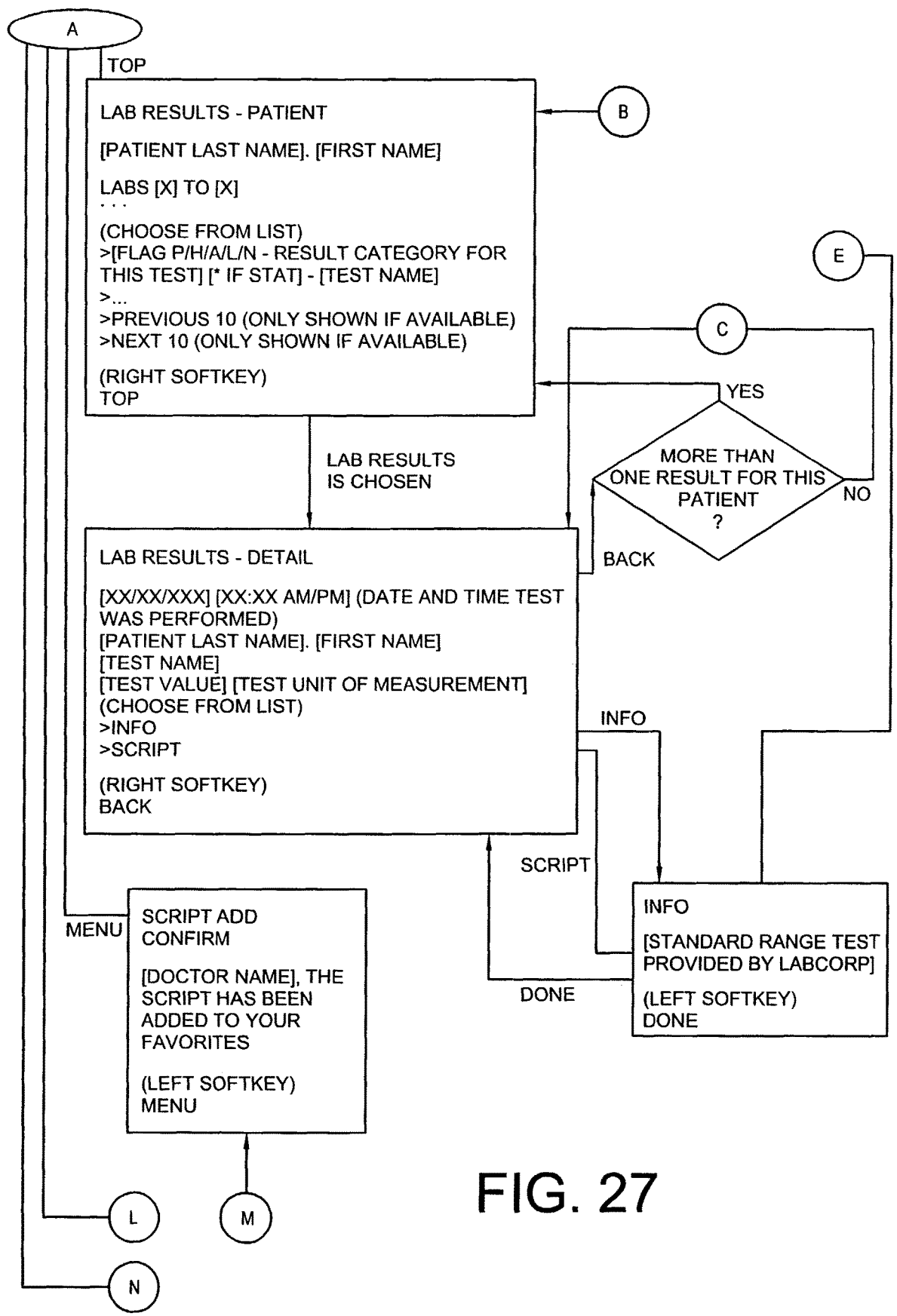

Turning to FIG. 17, the select lab data is displayed. This includes the date/time of the test, the patient's name, the name of the test performed, and the exact test value. The physician may also select "Range" to receive information that defines a standard or normal range for the displayed test. Also, at this stage, the physician may select "Script" to write and submit to a pharmacy a prescription for the patient as described below (see also FIG. 27).

Figure 18:
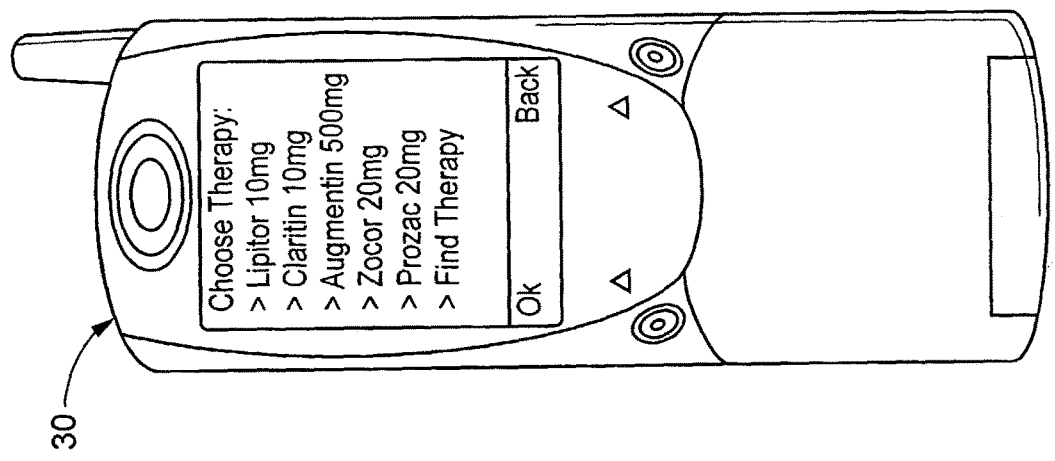
Figure 20:
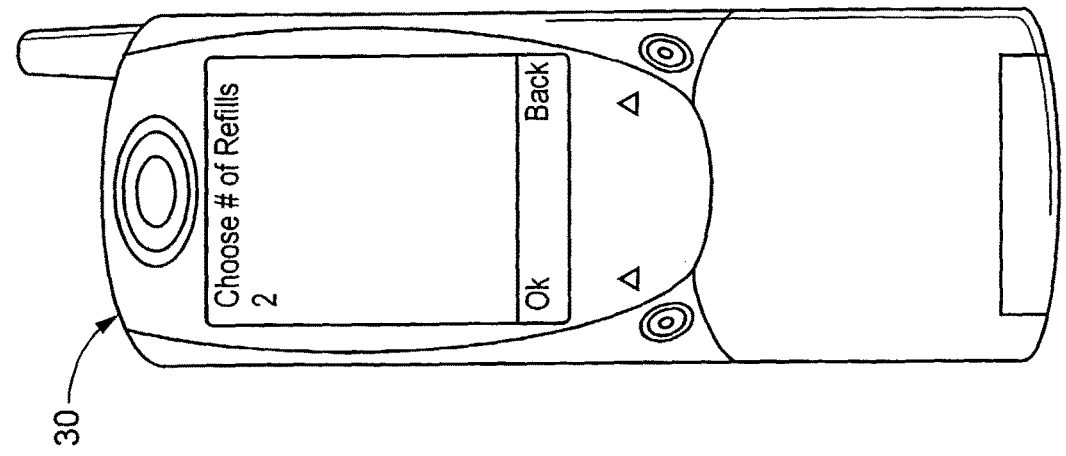
Figure 28:
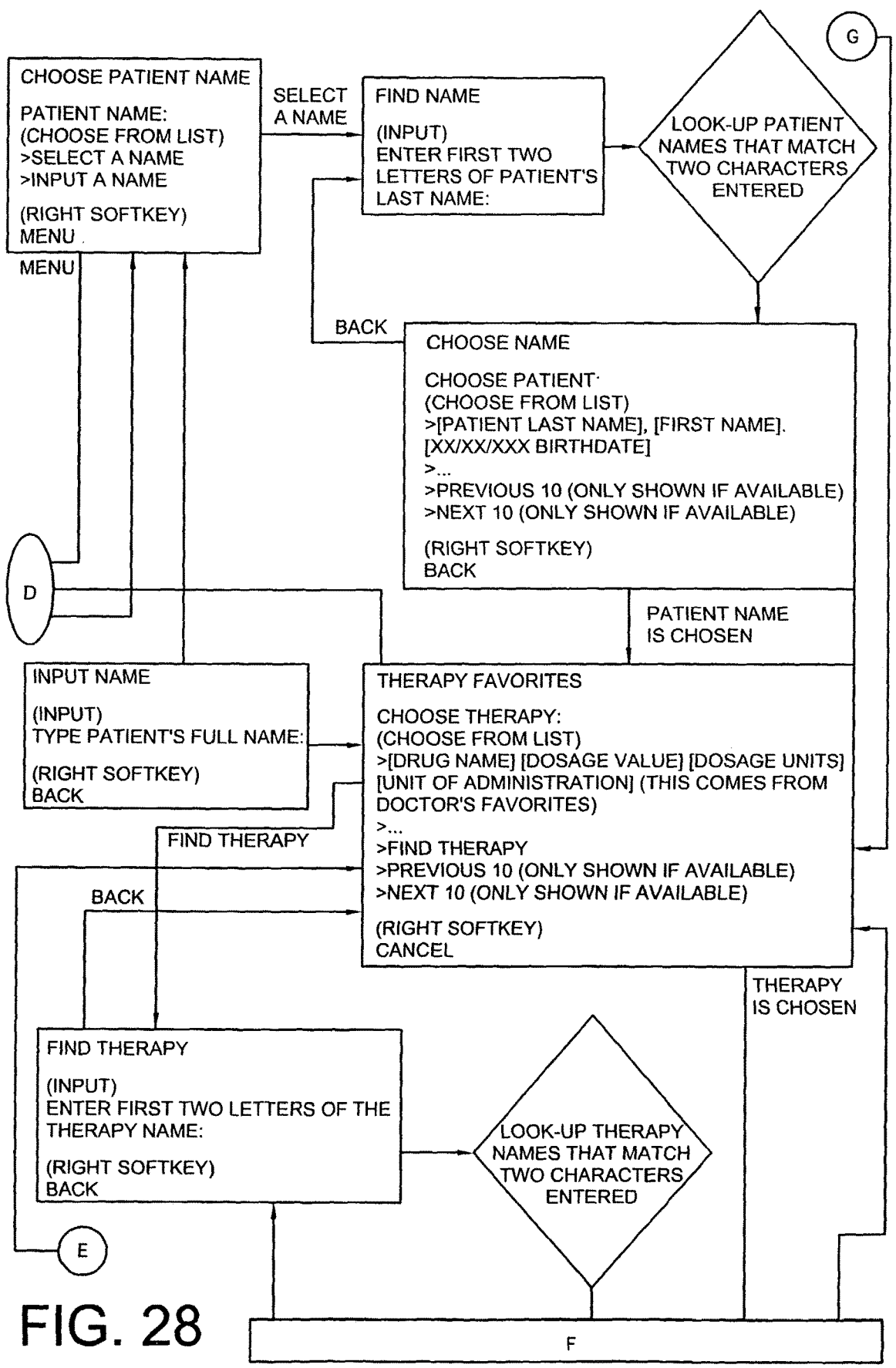
Figure 29:
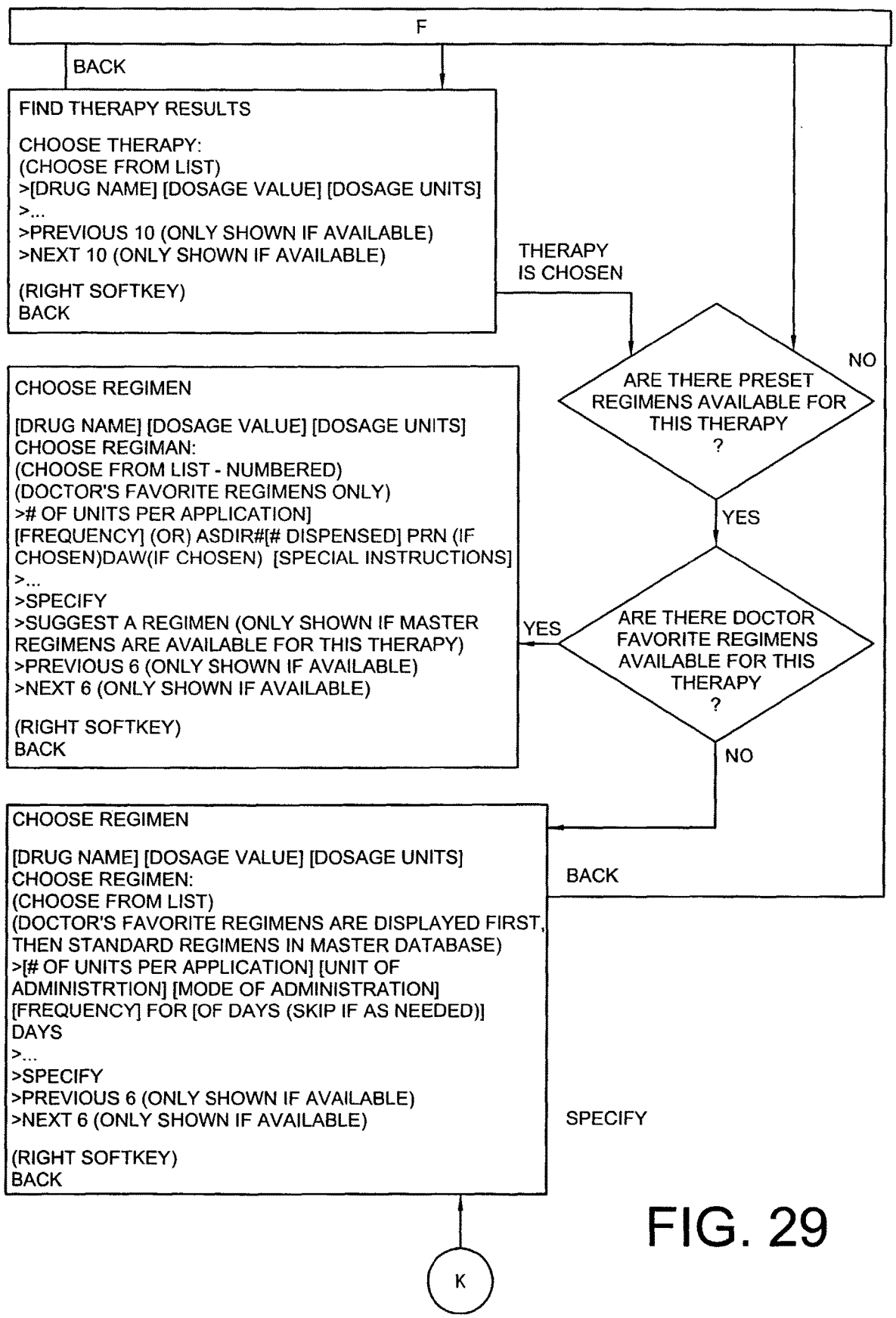
Figure 33:
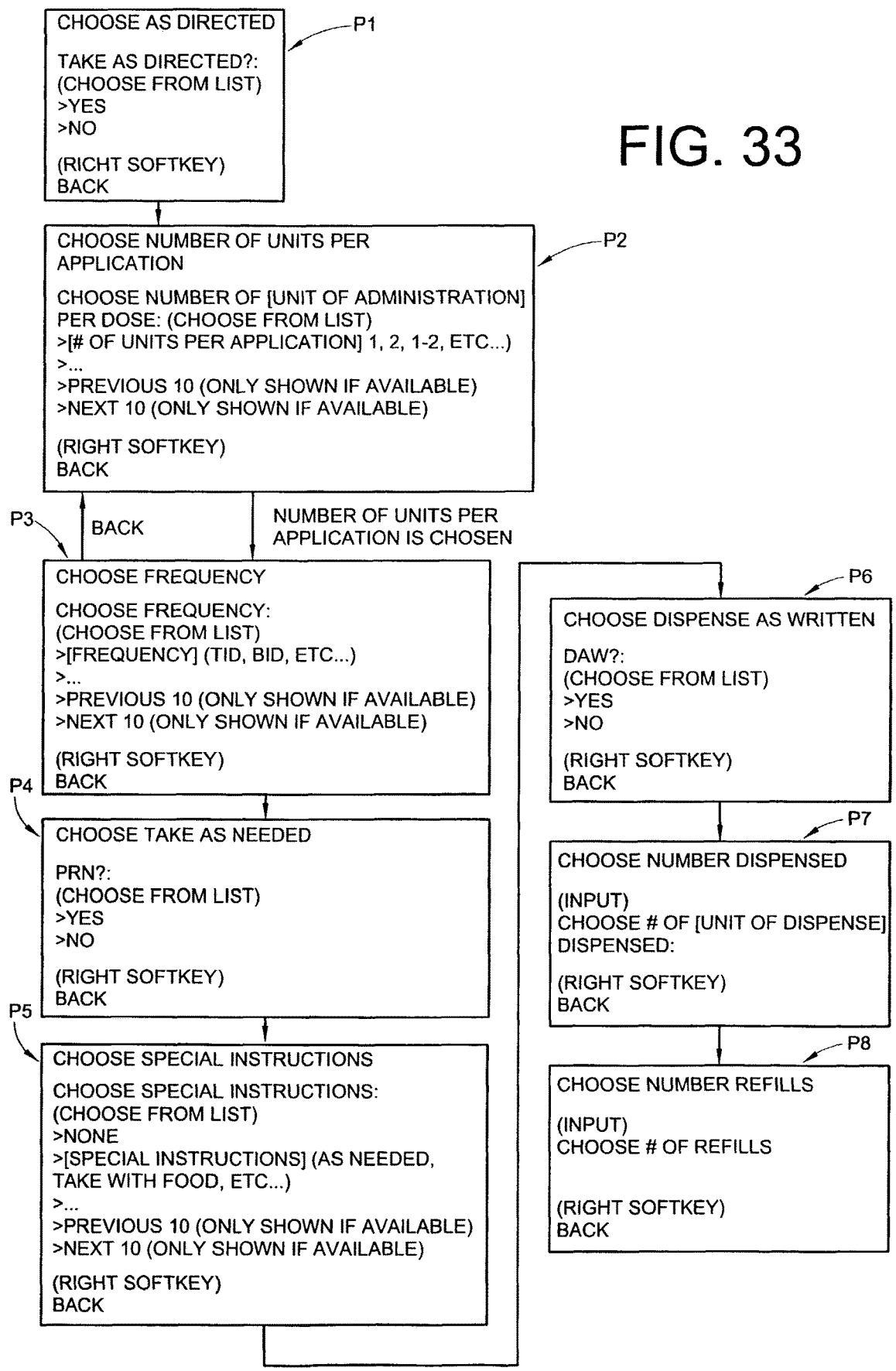

FIG. 18 illustrates the result when the physician selects the "Script" option. The physician is presented with a list of favorite (most commonly prescribed) therapies (drugs) for conditions related to the lab results reviewed by the physician immediately prior to this stage. The physician may select a therapy from the list or may select "Find Therapy" to search for others. Here, the physician selects "Claritin 10 mg" and is presented with the regimen data shown in FIG. 19. The physician selects or inputs the desired regimen at this stage and, as shown in FIG. 20, is prompted to input the number of refills. As illustrated in FIG. 33, it is most preferred that the physician be presented with multiple prompts on the display 32, such as those shown at P1-P8, and that the physician respond to each prompt P1-P8 as desired to develop the regimen using the input buttons 34 or other input means (see also FIGS. 28-29).

Figure 21:
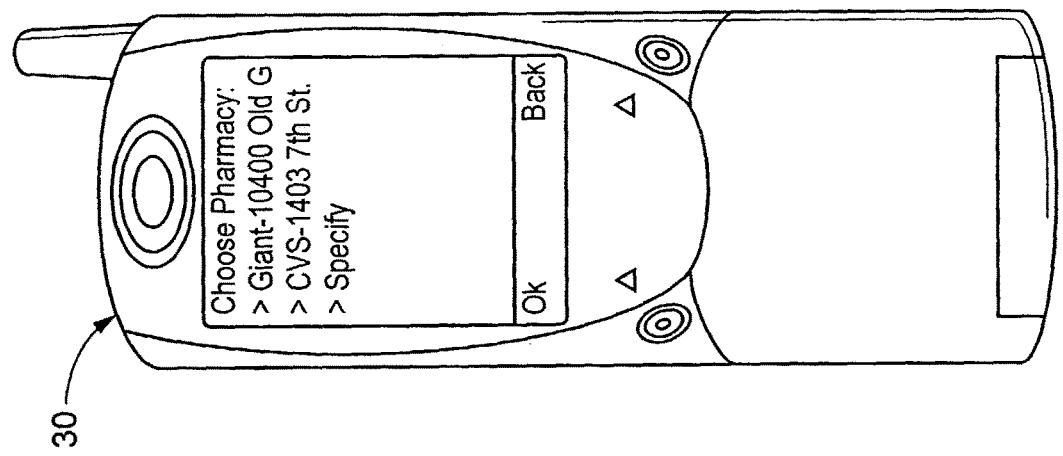
Figure 30:
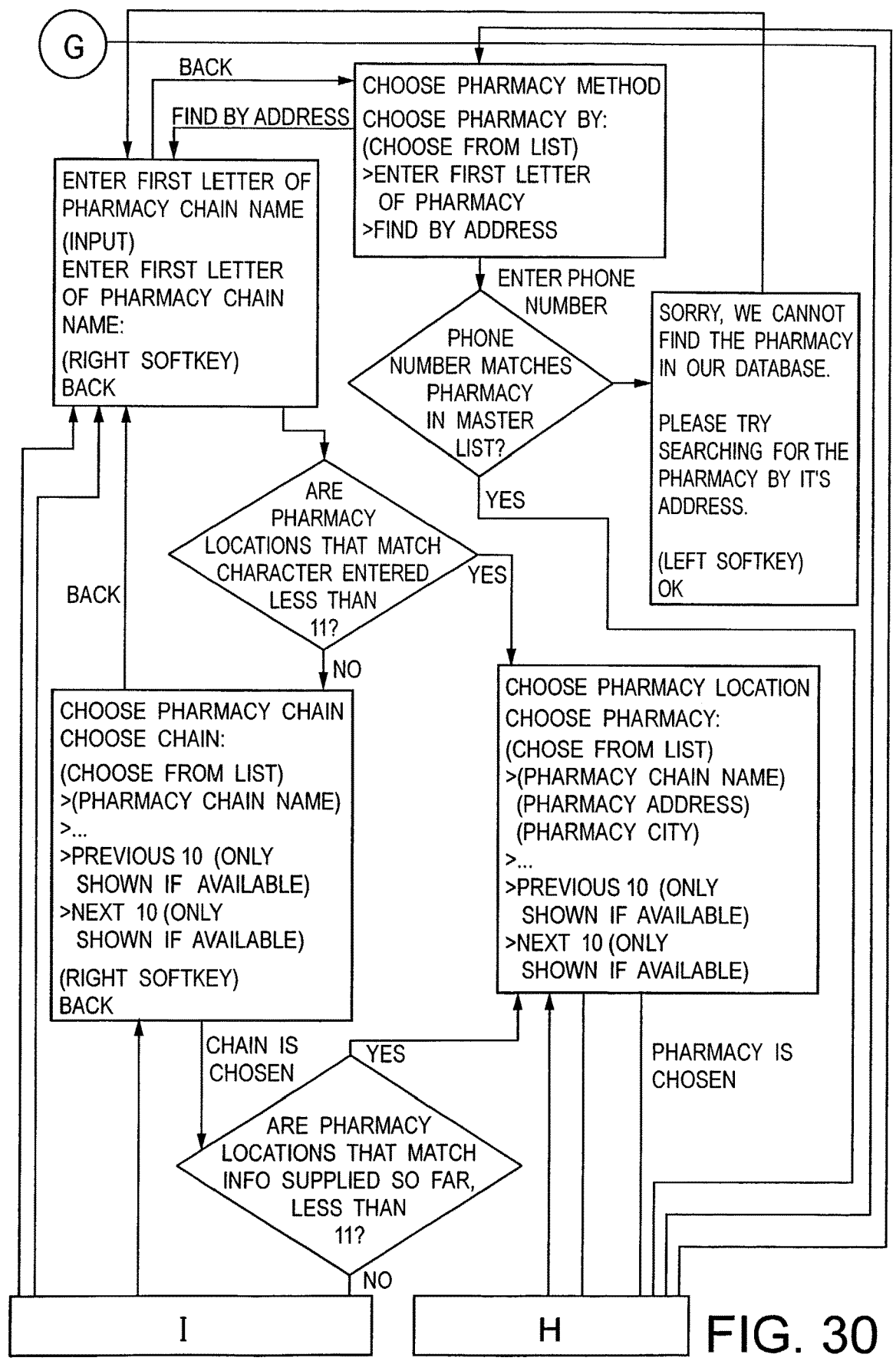
Figure 32:
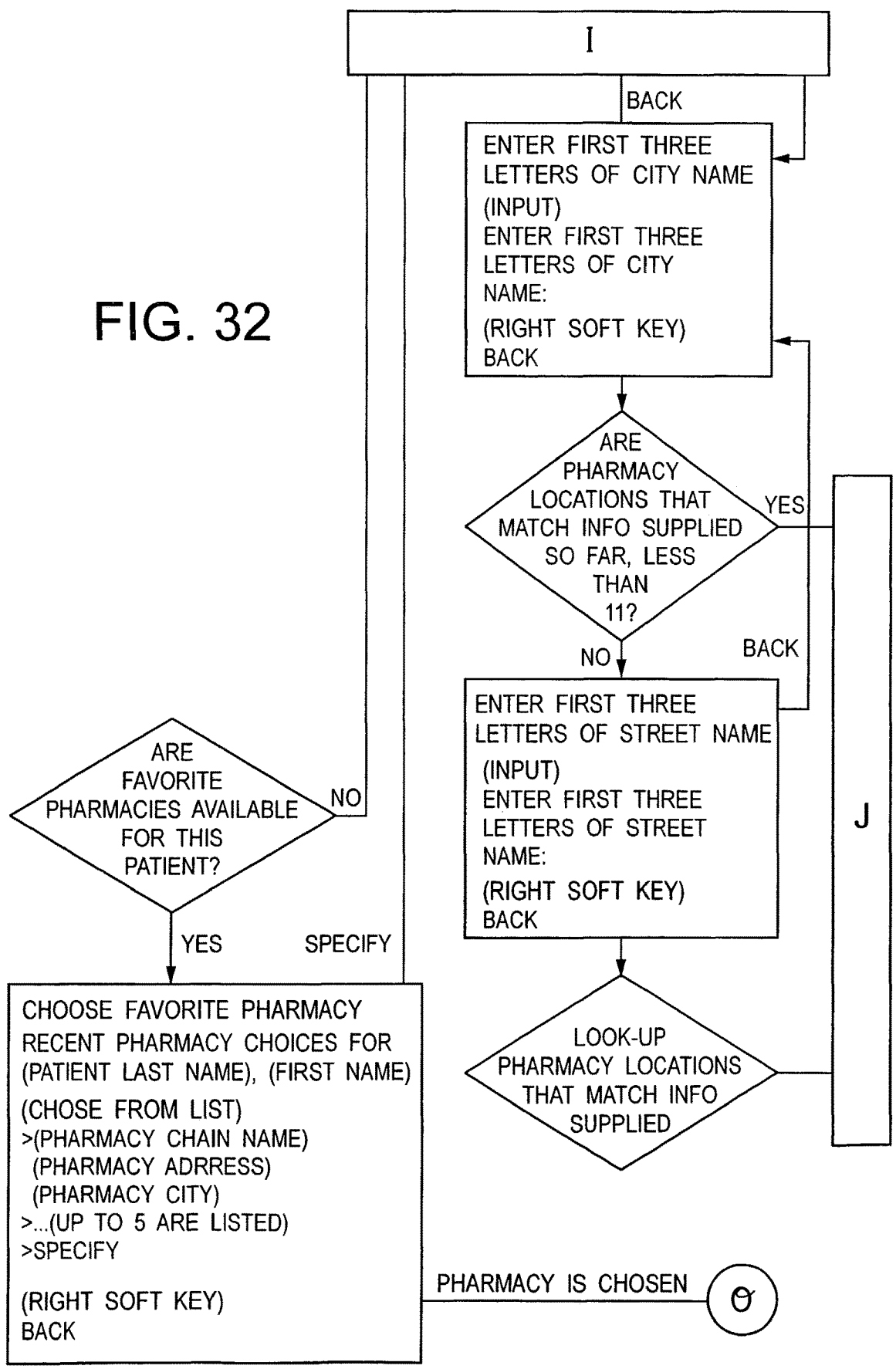

To submit the prescription to a pharmacy, the physician is presented with the data shown in FIG. 21. If the physician has written prescriptions for the subject patient previously, the previously used pharmacy or pharmacies are displayed and may be selected (see also FIG. 32). Otherwise, the physician inputs the desired pharmacy by phone number, address, or the physician may select a pharmacy from a predefined list of local pharmacies (see also FIG. 30).

Figure 22:
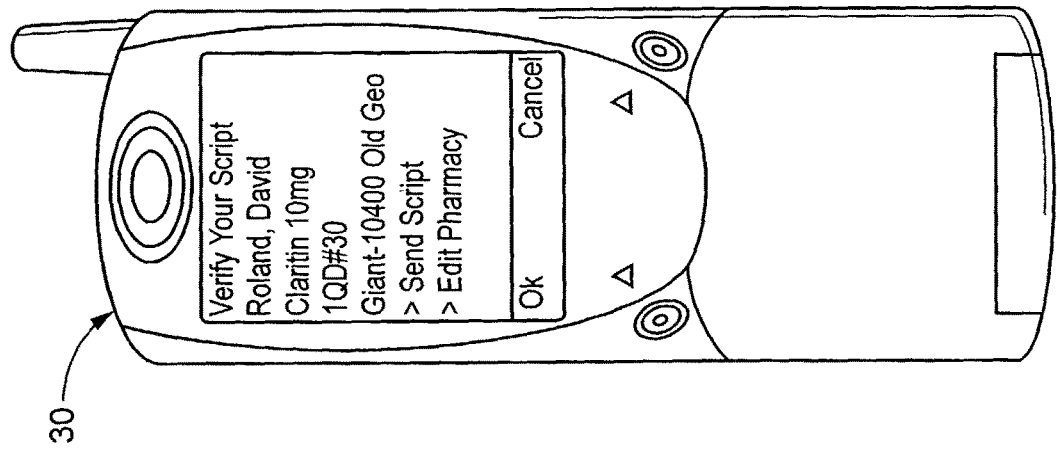
Figure 31:
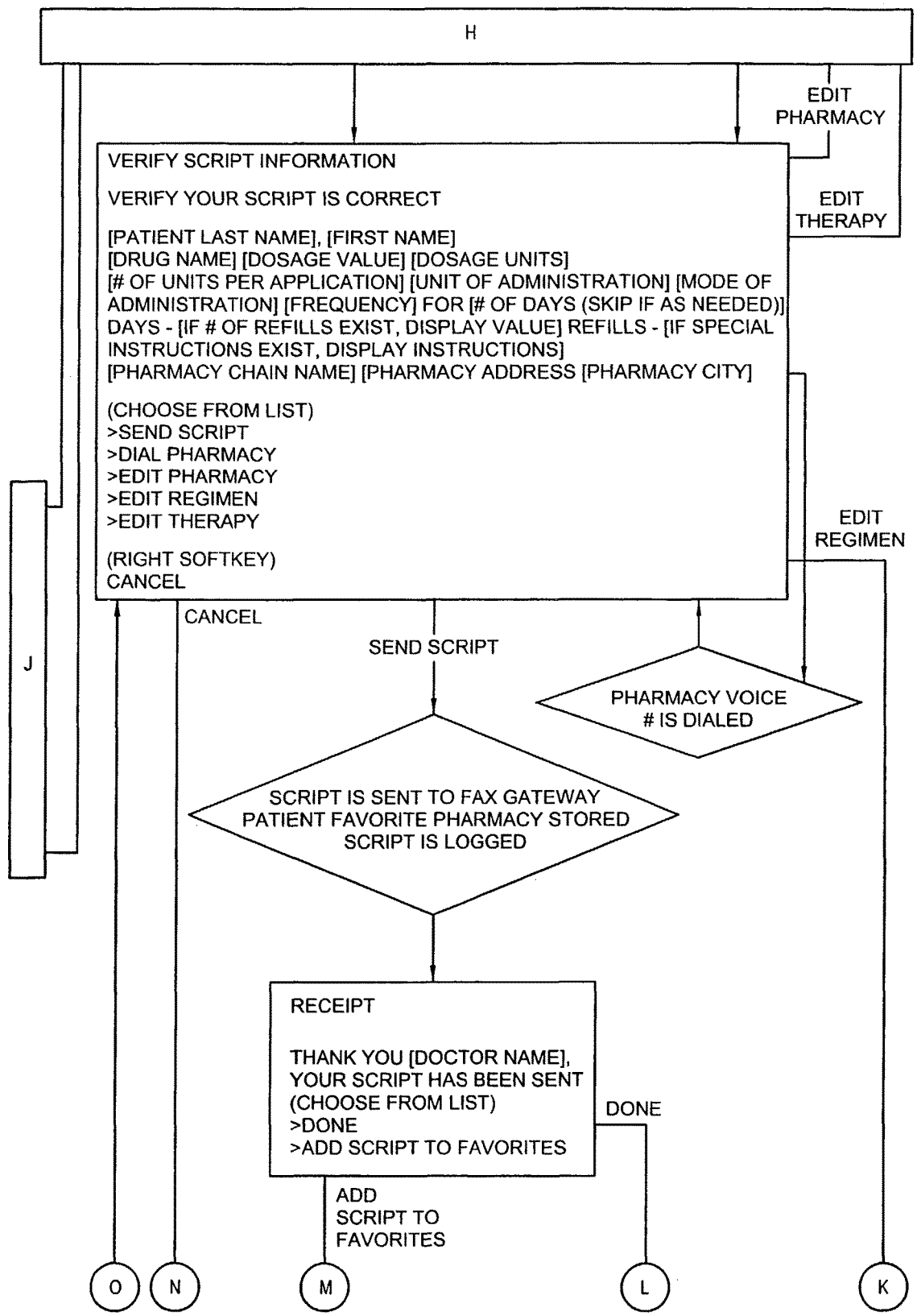

As shown in FIG. 22, the written prescription and selected pharmacy are displayed to the physician and he/she is required to verify same. At this stage, the physician may select "Send Script" to send the prescription to the pharmacy. Alternatively, the physician can edit previously entered information. Of course, at any stage, the physician is able to use to telephone 30 to send receive voice data, and he/she may prefer to submit prescriptions in this manner (see also FIG. 31).

Figure 25:
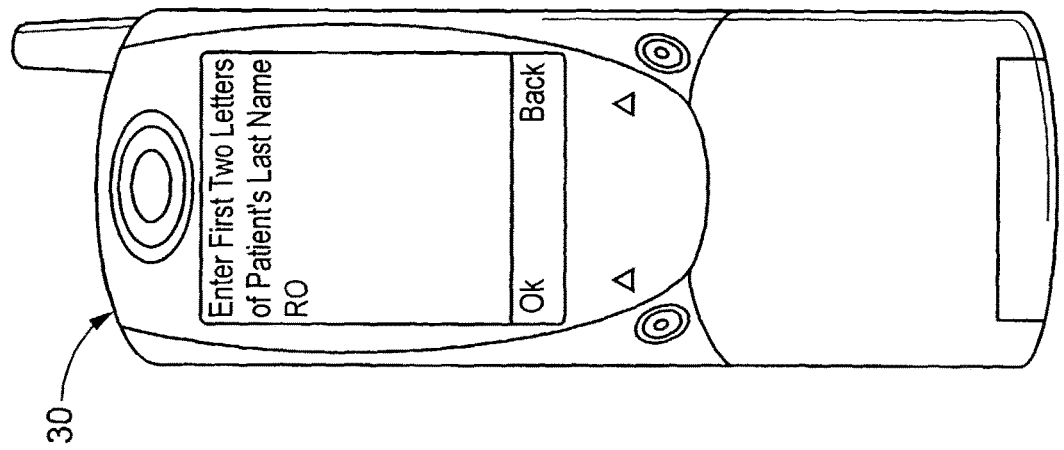
Figure 24:
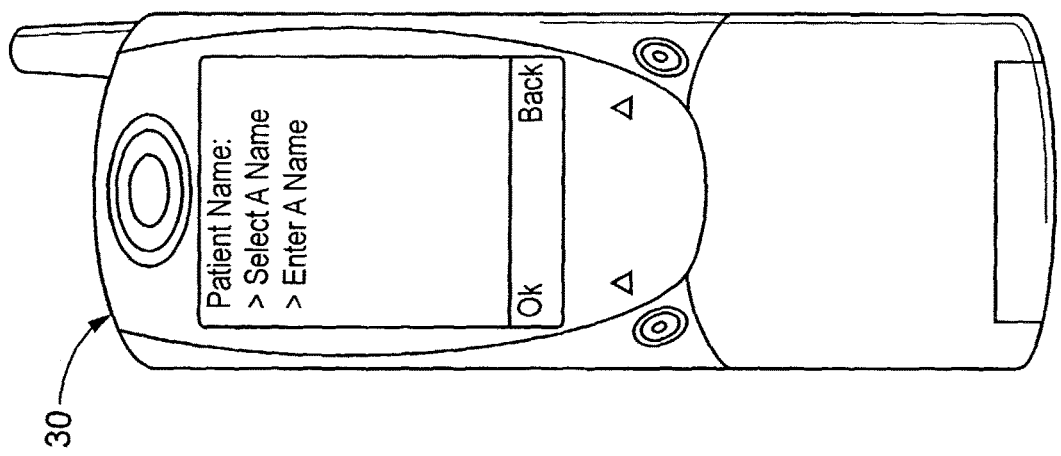
Figure 23:
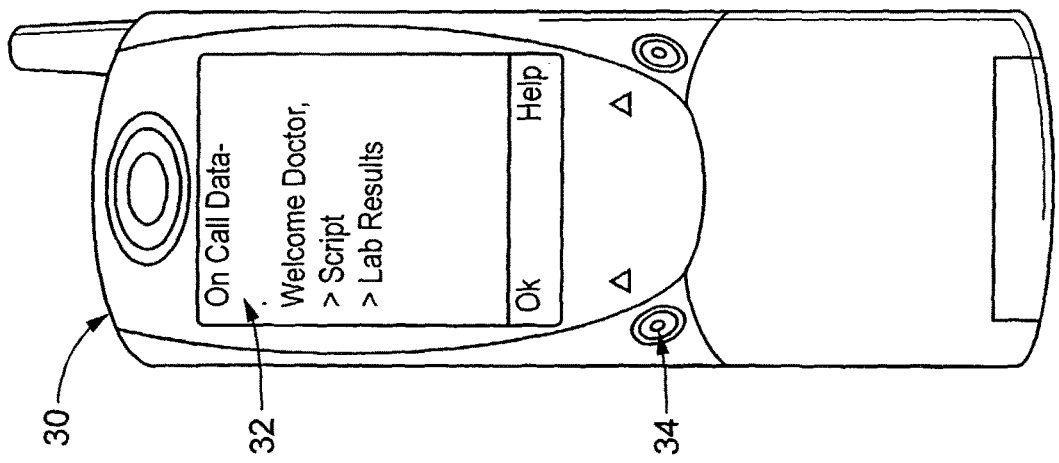

FIG. 23 again illustrates the welcome message displayed to a physician using the mobile device 30. The physician selects the option "Script" at this stage to immediately write and submit a prescription in accordance with the steps disclosed above. In such case, the physician must select from a list or enter a patient name as shown in FIG. 24. If the physician chooses to enter a name, he/she may enter only a portion thereof (FIG. 25) at which time a list of potentially matching patient names is displayed to the physician. The physician may then select the desired patient from the list. Following this, the procedure is in accordance with that described above in relation to FIGS. 18-22.

The invention has been described with reference to preferred embodiments. Modifications and alterations will occur to others upon a reading and understanding of the preceding specification. It is intended that the invention be construed as including all such modifications and alterations.

Having thus described the preferred embodiments, what is claimed is:

1. A method for physician use of a portable communications device to prepare and submit a prescription, said method comprising:
   receiving, by the portable communications device, a notification signal from a medical data server indicative of available medical test data in real-time;
   generating, via a display of the portable communications device, a user interface indicative of the availability of the medical test data responsive to the notification signal;
   retrieving, by the portable communications device from the medical data server, medical test data having test results for a plurality of medical tests for a patient associated with the notification signal responsive to an input received at the portable communications device;
   receiving, from the medical data server, at least one of the plurality of medical tests associated with the notification signal adapted for display on the portable communications device, wherein the portable communications device includes a limited screen size and a limited buffer size;

displaying, on the user interface of the portable communications device, the at least one of the plurality of medical tests for the patient associated with the notification signal;

receiving a comparison of each test result with a data range which determines severity and the data range defines normal standard test data results;

displaying, via the user interface of the portable communications device, a list of the compared test results ranked in order of severity via an Internet browser of said portable communications device;

receiving a request to generate a prescription for the patient after displaying the list of the test results;

displaying, via the user interface of the portable communications device, a list of drugs in response to the request using said portable communications device;

receiving, via the user interface of said portable communications device, input from an associated physician relating to a drug selected from said list of drugs;

displaying, via the user interface of said portable communications device, at least one predefined default electronic prescription for said selected drug, the at least one predefined default electronic prescription including identification of a drug, an amount of the drug, and dosing information for a patient, the dosing information identifying the frequency with which the patient takes the drug;

receiving, via the user interface of said portable communications device, input that one of: (i) accepts one of said at least one predefined default electronic prescriptions; (ii) modifies one of said at least one of said predefined default electronic prescription, or (iii) generates at least one electronic prescription that is not predefined;

sending one of said accepted, modified, or generated electronic prescriptions to a pharmacy using said portable communications device; and periodically receiving a reminder message when the sent electronic prescription requires that the patient submit to additional lab testing.

2. The method as set forth in claim 1, wherein the received medical test data includes test results for a plurality of patients, and the medical tests are ordered by the physician, and the displayed list includes the compared test results for the plurality of patients.

3. The method as set forth in claim 1, wherein said sending step comprises:

displaying, via said Internet browser, to said physician, a list of pharmacies previously used by the patient;

securely receiving input from said physician by way of said portable communication device that indicates one of said pharmacies selected from said list to which said physician desires to submit a prescription;

electronically transmitting said one of said accepted, modified, and generated electronic prescriptions securely to said selected pharmacy system.

4. The method as set forth in claim 3, further comprising:

after a predetermined period of time, receiving a compliance reply message from the pharmacy that indicates whether said patient has filled, re-filled, or not filled said electronic prescription; and displaying the received compliance message to said physician.

5. The method as set forth in claim 1, further including:

evaluating the received electronic prescription with one or more of a predetermined value for said selected drug, a patient history, a contraindication, a medication history, and a drug interaction.

6. The method as set forth in claim 5, further including:

displaying to said physician one or more prescription options when a prescribed dosage level exceeds said predetermined value, or is not recommended in view of the patient history, the contraindication, the medication cost or the drug interaction.

7. The method as set forth claim in claim 1, wherein said compared test results are ranked in order of decreasing test result severity for said patient, the test result severities including high results, low results, stat, and panic.

8. The method as set forth in claim 1, wherein the receiving by said portable communications device input from said physician modifies one of said at least one of said predefined default electronic prescription.

9. The method as set forth in claim 1, further including:

evaluating the received electronic prescription with all of a predetermined value for said selected drug, a patient history, a contraindication, a medication history, and a drug interaction; and displaying to said physician one or more prescription options when a prescribed dosage level exceeds said predetermined value, or is not recommended in view of the patient history, the contraindication, the medication cost or the drug interaction.

10. The method as set forth in claim 1, further comprising:

based the received comparisons, indicating a lab result of the patient as stat; and in response to the indication of stat, displaying a list of patients with the name of the patient whose lab result was indicated as stat before all other patients on the list.

11. The method as set forth in claim 1, further comprising:

in response to a determination that said physician typically specifies dispense as written (DAW), presenting a DAW option as a default.

12. The method as set forth in claim 1, further comprising:

storing, on a medical data server, a physician's preference for lab test result output format;

wherein the displaying to the physician the list of the compared test results further comprises displaying the compared test results in the output format stored on the medical data server.

13. The method as set forth in claim 1, further comprising:

transmitting a compliance request message to the pharmacy;

receiving a compliance reply message from the pharmacy that indicates whether said patient has filled or re-filled said electronic prescription; and displaying on said portable communications device the received compliance message.

14. The method as set forth in claim 1, further comprising:

displaying on said portable communications device one of: (i) a first list comprising names of a plurality of different patients for which medical test data are available have been sent to said portable communications device; and, (ii) a second list comprising names of a plurality of different tests for which medical test data have been sent to said portable communications device.

15. A method of electronic prescription, performed by one or more processors, comprising:

receiving, by an Internet browser capable device having a limited screen size and a limited buffer size, a notification signal from a medical data server indicative of available medical test data in real-time;

generating, via a display of the Internet browser capable device, a user interface indicative of the availability of the medical test data responsive to the notification signal;

receiving medical test data having medical test results related to at least one patient via secure data transmission to the Internet browser capable device, said medical test data generated by at least one medical laboratory, adapted for display on the Internet browser capable device and associated with the notification signal responsive to an input received via the user interface;

displaying test results ranked by severity on the Internet browser capable device, and the severity determined by comparing each test result with a data range;

receiving a generated, electronic prescription based at least in part on a selected one of the displayed test results and displaying the generated electronic prescription on the Internet browser capable device;

sending the electronic prescription from the Internet browser capable device directly to a pharmacy computer; and recommending one or more lab tests based at least in part upon the sent electronic prescription.

16. The method as set forth in claim 15, wherein said step of receiving a generated, electronic prescription comprises:

receiving from said Internet browser capable device input from said user relating to a drug selected from a displayed list of drugs that said user desires to prescribe;

displaying, via said Internet browser capable device, to said user at least one predefined default electronic prescription for said selected drug, the at least one predefined default electronic prescription including identification of a drug and dosing information for a patient, the dosing information identifying the frequency with which the patient takes the drug;

receiving from said Internet browser capable device input from said user that one of: (i) accepts said predefined default electronic prescription; (ii) modifies said predefined default electronic prescription, and (iii) generates at least one electronic prescription that is not predefined.

17. The method as set forth in claim 15, further comprising:

after a predetermined period of time, receiving a compliance reply message from the pharmacy that indicates whether said patient has filled, re-filled, or not filled said electronic prescription; and displaying, via said Internet browser capable device, the received compliance message to a user.

18. The method as set forth in claim 15, further including:
selecting one of the one or more recommended lab tests from said list that is generated based at least in part upon the electronic prescription.

19. The method as set forth in claim 15, wherein tests corresponding to the medical test data are ranked in order of decreasing test result severity for all patient names and all tests, respectively.

20. The method as set forth in claim 16, wherein the list of drugs is generated based on at least one of a patient history, a contraindication and a drug interaction.

21. The method as set forth in claim 15, further including:
evaluating the electronic prescription with one or more of a predetermined value for a drug corresponding to the electronic prescription, a patient history, a contraindication, a medication cost, a medication history, and a drug interaction.

22. The method as set forth in claim 21, further including:
displaying to a physician one or more prescription options when a prescribed dosage level exceeds said predetermined value, or is not recommended in view of the patient history, the contraindication, the medication cost or the drug interaction.

23. The method as set forth in claim 15, further including:
in response to the electronic prescription requiring the patient to undergo additional testing, transmitting at least one notification to the Internet browser capable device recommending one or more lab tests based at least in part upon the electronic prescription.

24. A method for creating an electronic prescription, said method comprising:

receiving, by an Internet browser on a portable device, a notification signal from a medical data server indicative of available medical test data in real-time;

generating, via a display of the portable device, a user interface in the Internet browser indicative of the availability of the medical test data responsive to the notification signal;

receiving medical test data related to at least one patient via secure data transmission to the Internet browser on the portable device, said medical test data generated by at least one medical laboratory and associated with the notification signal responsive to an input received via the user interface;

displaying, via the display of the portable device, the medical test data, wherein said medical test data is adapted for display on the portable device in accordance with a limited screen size and a limited buffer size of the portable device;

generating an electronic prescription;

in response to the electronic prescription requiring the patient to undergo additional testing, transmitting at least one notification to the Internet browser recommending one or more lab tests based at least in part upon the electronic prescription;

providing a patient access to at least one of lab test results, the medical test data, and a treatment regimen, wherein the access is provided via a network connection to a medical data server by a fixed or portable device of the patient.

25. A method as set forth in claim 24, further comprising storing, on the medical data server, a physician's preference for lab test result output format.

26. A method as set forth in claim 24, further comprising displaying, to a physician, a list of most commonly prescribed drugs for conditions related to the lab test results.

27. An electronic device programmed to perform the method of claim 24.

28. A method comprising:

displaying, via an Internet browser of a communications device, to a physician a list of drugs, wherein said communications device is an Internet browser on a portable device;

receiving from said communications device input from said physician relating to a drug selected from said list that said physician desires to prescribe;

displaying, via the Internet browser, to said physician at least one predefined default electronic prescription for said selected drug, wherein said at least one predefined default electronic prescription for said selected drug is adapted for display on the portable device having a limited screen size and a limited buffer size;

receiving from said communications device input from said physician that one of: (i) accepts one of said at least one predefined default electronic prescription; (ii) modifies one of said at least one of said predefined default electronic prescription, or (iii) generates at least one electronic prescription that is not predefined, wherein the at least one predefined default electronic prescription including identification of a drug and dosing information for a patient, the dosing information identifying the frequency with which the patient takes the drug;

sending one of said accepted, modified, or generated electronic prescriptions to a pharmacy system from said communications device; and in response to the sent one of said accepted, modified, or generated electronic prescriptions requiring that the patient submit to additional lab testing, periodically receiving a reminder message.

29. The method as set forth in claim 28, wherein the sending step comprises:
displaying a list of pharmacies in response to entry of a first letter of a pharmacy name and the generated list includes pharmacies with names that begin with the entered first letter.

30. The method as set forth in claim 28, wherein said sending step comprises:
displaying, via said Internet browser, a list of pharmacies to said physician generated from entry of a first letter of names of pharmacies;
securely receiving input from said physician by way of said communication device that indicates one of said pharmacies selected from said list to which said physician desires to submit a prescription;
electronically transmitting said one of said accepted, modified, or generated electronic prescriptions securely to said selected pharmacy system.

31. The method as set forth in claim 28, further comprising:
receiving medical test data having test results for a plurality of medical tests for a plurality of patients, and the medical tests ordered by said physician;
comparing each test result with a data range to determine severity of a diagnosis; and
displaying the compared test results in order of severity to said physician on the Internet browser.

32. The method as set forth in claim 28, further comprising:
after a predetermined period of time, receiving a compliance reply message from the pharmacy that indicates whether said patient has filled, re-filled, or not filled said electronic prescription; and
displaying, via said Internet browser on the portable device, the received compliance message to said physician.

33. The method as set forth in claim 28, further including:
evaluating the received electronic prescription with one or more of a predetermined value for said selected drug, a patient history, a contraindication, a medication cost, a medication history, and a drug interaction.

34. The method as set forth in claim 33, further including:
displaying to said physician one or more prescription options when a prescribed dosage level exceeds said predetermined value, or is not recommended in view of the patient history, the contraindication, the medication cost or the drug interaction.

35. An apparatus for electronically transmitting a prescription, comprising:
an electronic device programmed to:
receive a notification signal from a medical data server indicative of available medical test data in real-time;
generate, on an Internet browser of a display of the electronic device, a user interface indicative of the availability of the medical test data responsive to the notification signal, wherein said user interface is adapted for display on the electronic device in accordance with a limited screen size and a limited buffer size associated with the electronic device;
display on the Internet browser of the display a list of available drugs based on the results of at least one medical test for a patient;
in response to selection of a drug from the list of available drugs, display on the Internet browser at least one predefined default electronic prescription for the selected drug;
in response to input from the user that accepts or modifies at least one predefined default electronic prescription, use the Internet browser to display a list of pharmacies;
in response to input from the user that indicates one of said pharmacies selected from the list, electronically transmit the at least one accepted or modified electronic prescription directly to the selected pharmacy system;
if the transmitted electronic prescription requires that the patient submit to additional lab testing, periodically receive a reminder message.

36. The apparatus as set forth in claim 35, wherein the list of pharmacies includes pharmacies of a first letter entered by the user.

37. The apparatus as set forth in claim 35, wherein the at least one predefined default electronic prescription includes identification of a drug and dosing information for a patient, the dosing information identifying the frequency with which the patient takes the drug.

* * * * *